(12) United States Patent
Yamakawa et al.

(10) Patent No.: US 9,420,986 B2
(45) Date of Patent: Aug. 23, 2016

(54) X-RAY CT APPARATUS AND X-RAY CT IMAGE PROCESSING METHOD

(71) Applicant: HITACHI MEDICAL CORPORATION, Tokyo (JP)

(72) Inventors: Keisuke Yamakawa, Tokyo (JP); Shinichi Kojima, Tokyo (JP)

(73) Assignee: HITACHI, LTD., Tokyo (JP)

( * ) Notice: Subject to any disclaimer, the term of this patent is extended or adjusted under 35 U.S.C. 154(b) by 64 days.

(21) Appl. No.: 14/408,576

(22) PCT Filed: Jul. 12, 2013

(86) PCT No.: PCT/JP2013/069206
§ 371 (c)(1),
(2) Date: Dec. 17, 2014

(87) PCT Pub. No.: WO2014/041889
PCT Pub. Date: Mar. 20, 2014

(65) Prior Publication Data
US 2015/0190106 A1    Jul. 9, 2015

(30) Foreign Application Priority Data
Sep. 13, 2012   (JP) .................................. 2012-201808

(51) Int. Cl.
*G06K 9/00*       (2006.01)
*A61B 6/00*       (2006.01)
(Continued)

(52) U.S. Cl.
CPC ............... *A61B 6/5235* (2013.01); *A61B 6/032* (2013.01); *A61B 6/5205* (2013.01);
(Continued)

(58) Field of Classification Search
USPC ......... 382/100, 103, 106–107, 128–134, 154, 382/162, 168, 173, 181, 220, 232, 254, 274, 382/276, 286–291, 305, 312; 378/4, 21, 20
See application file for complete search history.

(56) References Cited

U.S. PATENT DOCUMENTS

2008/0240335 A1*  10/2008  Manjeshwar ......... A61B 6/032
                                                 378/4
2009/0225934 A1*  9/2009   Hugg ..................... A61B 6/032
                                                 378/20
(Continued)

FOREIGN PATENT DOCUMENTS

JP    2004-65706 A    3/2004
JP    2006-25868 A    2/2006
(Continued)

OTHER PUBLICATIONS

International Search Report from International Application No. PCT/JP13/069206 mailed on Oct. 15, 2013.
(Continued)

*Primary Examiner* — Seyed Azarian
(74) *Attorney, Agent, or Firm* — Brundidge & Stanger, P.C.

(57) ABSTRACT

The present invention is directed to improve the precision of a CT image of a local region (small FOV image) that is obtained by applying the extensive reconstruction technique to the iterative approximate reconstruction method. A first CT image relating to a first reconstruction range is reconstructed from the projection data of a subject, the projection data being detected by the X-ray detector of the X-ray CT apparatus, and the first CT image is corrected iteratively so that the first calculated projection data obtained from the first CT image according to projection calculation, becomes equal to the projection data of the subject. The first CT image thus iteratively corrected is used to extract local measured projection data in association with the second reconstruction range. A second CT image is reconstructed in the second reconstruction range and the second CT image is iteratively corrected so that the extracted local measured projection data becomes equal to the second calculated projection data that is obtained from the second CT image according to the projection calculation.

13 Claims, 17 Drawing Sheets

(51) Int. Cl.
*A61B 6/03* (2006.01)
*G06T 11/00* (2006.01)

(52) U.S. Cl.
CPC ............ *A61B 6/5258* (2013.01); *G06T 11/005* (2013.01); *A61B 6/465* (2013.01); *G06T 2207/10081* (2013.01); *G06T 2207/20182* (2013.01)

(56) References Cited

U.S. PATENT DOCUMENTS

| 2010/0246751 A1* | 9/2010 | Bruder ................... G06T 11/006 378/4 |
| 2013/0028500 A1* | 1/2013 | Takahashi .............. A61B 6/032 382/132 |
| 2013/0272490 A1* | 10/2013 | Noguchi .............. A61B 6/4441 378/4 |

FOREIGN PATENT DOCUMENTS

| JP | 2011-177396 A | 9/2011 |
| WO | 2011/122613 A1 | 10/2011 |
| WO | 2012/081245 A1 | 6/2012 |

OTHER PUBLICATIONS

Andy Ziegler et al., "Interative reconstruction of a region of interest for transmission tomography", Med. Phys. 35(4), p. 1317-1327, 2008.

English translated International Preliminary Report mailed on Mar. 26, 2015.

* cited by examiner

FIG. 4
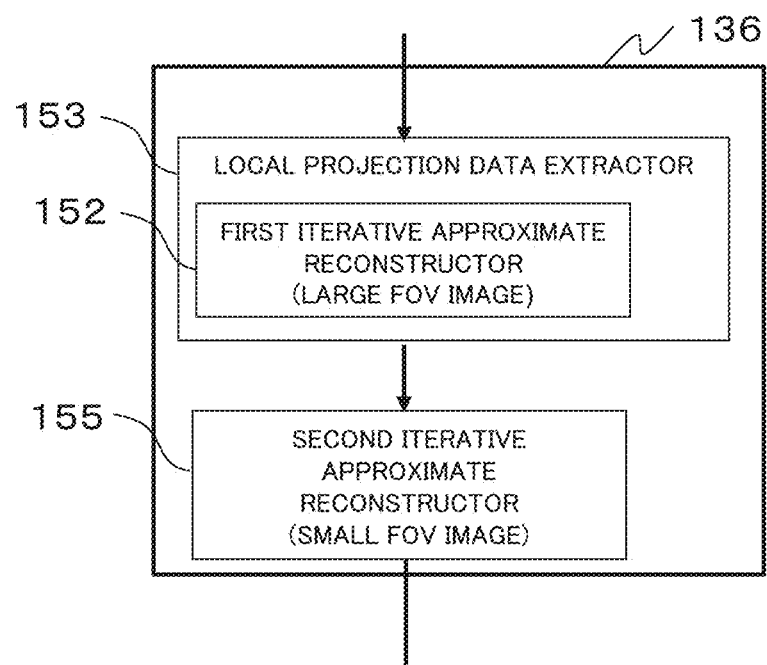
(a)
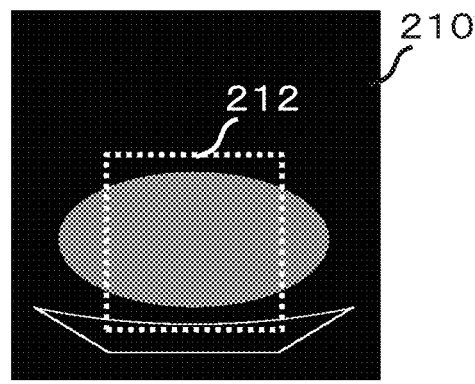
(b)

FIG. 11
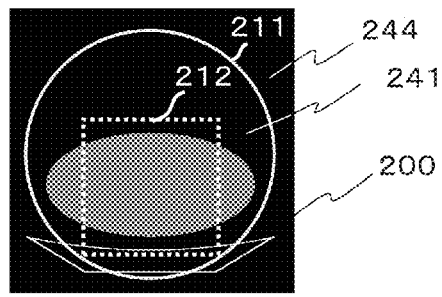
(a) ORIGINAL IMAGE
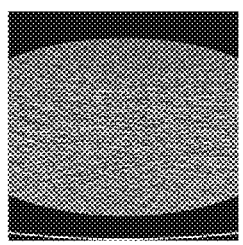
(b) FBP METHOD
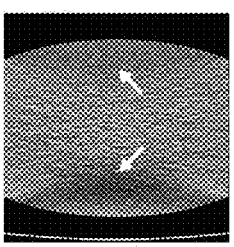
(c) W(i): NO CORRECTIONS
Wr(i): STATISTICAL VALUE
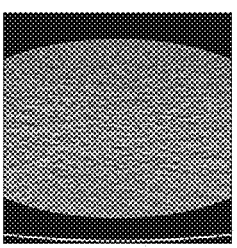
(d) W(i): STATISTICAL VALUE
Wr(i): STATISTICAL VALUE
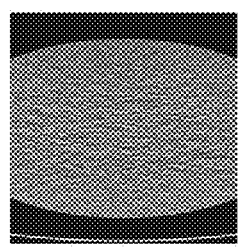
(e) W(i): CONSTANT VALUE
Wr(i): STATISTICAL VALUE
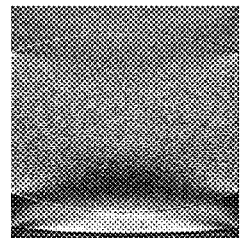
(f) (c)−(b)
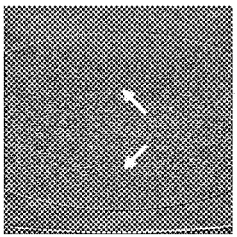
(g) (d)−(b)
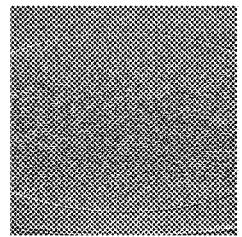
(h) (e)−(b)
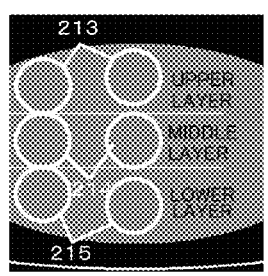
(i) POSITIONS OF ROI FOR EVALUATION
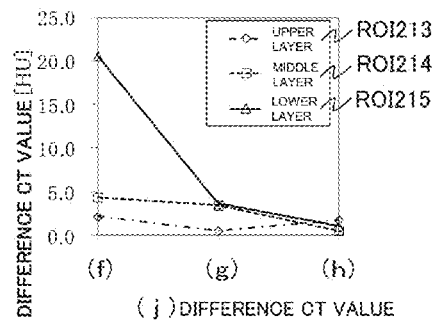
(j) DIFFERENCE CT VALUE FIG. 13
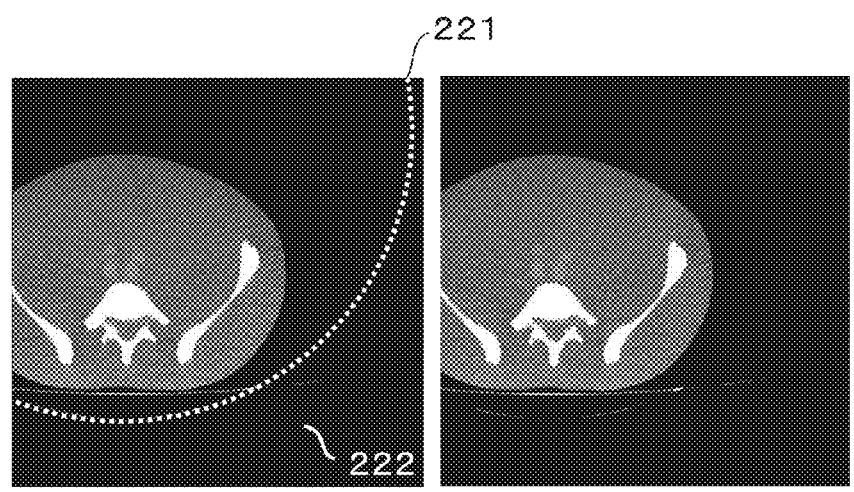
(a) W( i ): CONSTANT VALUE
Wr( i ): STATISTICAL VALUE
(b) W( i ): CONSTANT VALUE
Wr( i ): STATISTICAL VALUE, CONSTANT VALUE
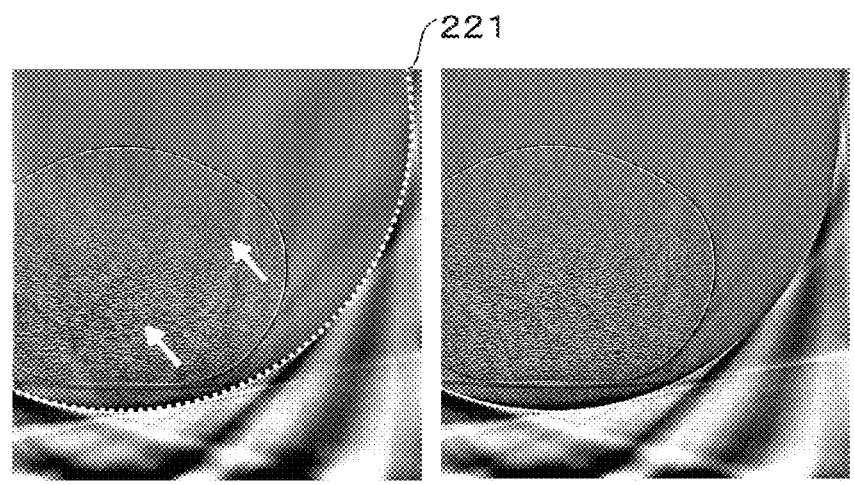
(c) (a)−FBP METHOD
(d) (b)−FBP METHOD FIG. 19
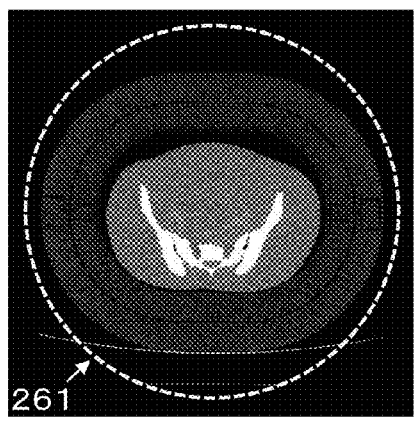
(a) W(i): STATISTICAL VALUE
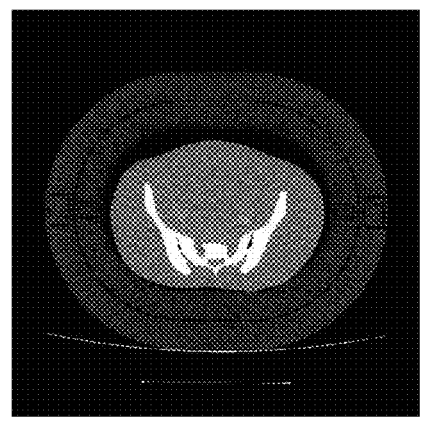
(b) W(i): STATISTICAL VALUE, CONSTANT VALUE
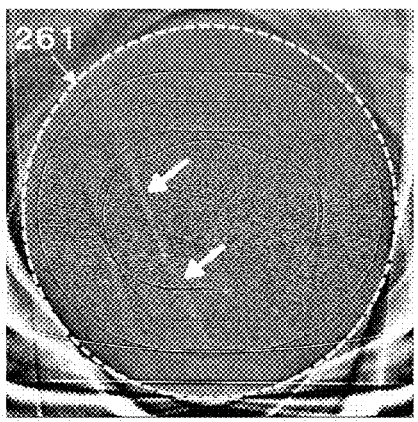
(c) (a)-FBP METHOD
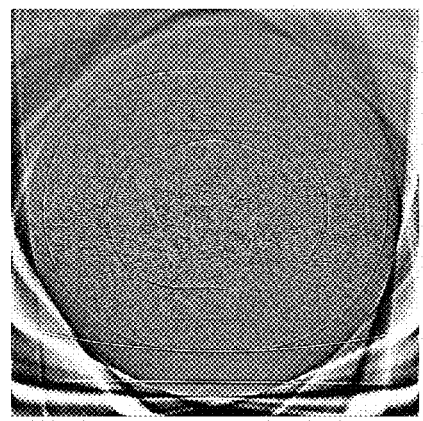
(d) (b)-FBP METHOD

X-RAY CT APPARATUS AND X-RAY CT IMAGE PROCESSING METHOD

TECHNICAL FIELD

The present invention relates to an X-ray CT apparatus, and also relates to an image generating technique that iteratively corrects a CT image, in such a manner that calculated projection data obtained by subjecting the CT image to a forward projection process becomes equal to measured projection data that is obtained by measurement.

BACKGROUND ART

An X-ray CT (Computed Tomography) apparatus calculates an X-ray absorption coefficient at each point from the measured projection data that is obtained by imaging a subject from multi-directions, and obtains as a tomographic image of a subject, an X-ray absorption coefficient distribution image (hereinafter, referred to as "CT image") made up of plural pixels. The CT image acquired through this apparatus allows a patient's disease condition to be diagnosed accurately and immediately in medical practice, and it is clinically effective. However, a constant amount of radiation exposure is unavoidable in order to acquire an image of high quality necessary for diagnosis by a doctor. On the other hand, if the radiation dose is lowered in order to implement low dose scanning, a noise ratio increases to the signals being detected, and a large amount of linear streak artifact and/or graininess noise may occur, causing erroneous diagnosis. Therefore, it is desired to reduce such streak artifact and noise in the low dose scanning, and to achieve compatibility between high-quality diagnosis and low dose scanning.

In view of the situation above, the Patent Document 1 describes that there is employed an iterative approximate reconstruction method to iteratively correct a CT image so as to satisfy the condition that the calculated projection data is equal to the measured projection data, and reduce the noise. In the iterative approximate reconstruction method, firstly, a reconstructing process is performed on the region for reconstruction (hereinafter, referred to as "FOV") including the subject, and an image (FOV image) is obtained. Next, projection data is calculated from the reconstructed image (FOV image) (hereinafter, referred to as "forward projection calculation"), and iterates the operation for correcting the CT image, in comparison to the aforementioned measured projection data. This may enhance the precision of the CT image within the FOV. The iterative approximate reconstruction method requires the condition that the FOV incorporates the subject therein, and therefore, if the correction of the subject is unrelated to the diagnosis, it may cause increase of the calculation amount.

As a publicly known analytical reconstruction method, an extensive reconstruction method is suggested to perform reconstruction operation on a local region, so as to reduce the calculation amount. In view of this, it is conceivable to apply the extensive reconstruction technique to the iterative approximate reconstruction method, and reduce the calculation amount. However, in the iterative approximate reconstruction method, it is difficult to perform the reconstruction operation only on the local region out of the measured projection data, and therefore, it is necessary to extract from the measured projection data, projection data being included in the local region (hereinafter, referred to as "local measured projection data").

The Non Patent Document 1 discloses a technique that applies the extensive reconstruction technique to the iterative approximate reconstruction method. This technique reconstructs a CT image on the FOV incorporating the subject with a table, a fixture, and the like (hereinafter, referred to as "large FOV image"). Next, an image of a background region other than the local region is extracted from the large FOV image, and thus extracted image of the background region is subjected to the forward projection calculation, thereby obtaining background projection data. Thus obtained background projection data is subtracted from the measured projection data, thereby extracting local measured projection data, and calculating the CT image of the local region (hereinafter, referred to as "small FOV image"). Accordingly, it is possible to apply the iterative approximate reconstruction method to the local measured projection data, and improve the precision of the small FOV image.

On the other hand, in the analytical reconstruction method, when data obtained at some projection angles fails to be measured on the periphery of the FOV, it is known that the precision of the CT image of the FOV is remarkably deteriorated (incomplete reconstruction). The Patent Document 2 advises to estimate the subject within the region where data is unmeasurable on the periphery of the FOV, thereby improving the precision of a CT value (X-ray absorption value) in the FOV image.

PRIOR ART DOCUMENT

Patent Document

Patent Document 1
Japanese Unexamined Patent Application Publication No. 2006-25868
Patent Document 2
Japanese Unexamined Patent Application Publication No. 2004-65706

Non Patent Document

Non Patent Document 1
Andy Ziegler, et al., "Iterative reconstruction of a region of interest for transmission tomography", Med. phys. 35(4), p. 1317-1327, 2008

DISCLOSURE OF THE INVENTION

Problem to be Solved by the Invention

When the extensive reconstruction technique is applied to the iterative approximate reconstruction method, the precision of the CT value of the small FOV image is dependent on the precision of the local measured projection data. Therefore, in order to enhance the precision of the CT value of the small FOV image, it is necessary to enhance the precision of the local measured projection data. A major factor for lowering the precision of the local measured projection data is considered to be deterioration of the CT value precision in the large FOV image. By way of example, the following things included in the large FOV image may be the factors; quantum noise, circuit noise, streak artifact, beam hardening effect, incomplete reconstruction due to data deficiency at the projection angle that is necessary for the reconstruction, errors in reference correction, and the like.

In order to improve the CT value precision of the large FOV image, it is conceivable that the technique of the aforementioned Patent Document 2 is applied to estimate the subject in the region where data on the periphery of the large FOV is unmeasurable. However, if the area or the volume of the subject increases in the region where the data is unmeasurable, the precision in estimating the CT value may be deteriorated.

An object of the present invention is to enhance the precision of the CT image in the local region (small FOV image) that is obtained when the extensive reconstruction technique is applied to the iterative approximate reconstruction method.

Means to Solve the Problem

In order to achieve the object above, according to the present invention, the first CT image of the first reconstruction range (FOV) is reconstructed from projection data of the subject that is detected by the X-ray detector of the X-ray CT apparatus, and the first CT image is used to extract from the measured projection data, local measured projection data in association with the second reconstruction range (FOV) within the first reconstruction range (FOV). In this situation, the first CT image is iteratively corrected so that the first calculated projection data obtained from the first CT image according to projection calculation, becomes equal to the projection data of the subject. With this configuration, it is possible to obtain the local measured projection data that is associated with the second reconstruction range (FOV) with a high degree of precision. Accordingly, the second CT image is corrected iteratively so as to allow the second CT image in association with the second reconstruction range (FOV) to be equal to the second local measured projection data, thereby obtaining a CT image of the local region with a high degree of precision.

Effect of the Invention

In the present invention, the first CT image is iteratively corrected so as to obtain local measured projection data, thereby obtaining the local measured projection data with a high degree of precision. Accordingly, it is possible to generate the second CT image of the local region, from the local measured projection data, with a high degree of precision.

BRIEF DESCRIPTION OF DRAWINGS

FIG. 4($a$) is a functional block diagram illustrating the functions of the reconstruction processor 136 in the first embodiment, and FIG. 4($b$) illustrates a large FOV and a small FOV;

FIG. 10($a$) illustrates a constant value weight and FIG. 10($b$) illustrates a statistical value weight;

FIG. 11($a$) to FIG. 11($h$) illustrate the calculation results of the reconstructed image in the second embodiment, and FIG. 11($i$) and FIG. 11($j$) illustrate evaluation results of the region of interest;

FIG. 13($a$) to FIG. 13($d$) illustrate calculation results of the reconstructed image in the third embodiment;

FIG. 19($a$) to FIG. 19($d$) illustrate calculation results of the reconstructed image in the sixth embodiment.

MODES FOR CARRYING OUT THE INVENTION

Figure 1:
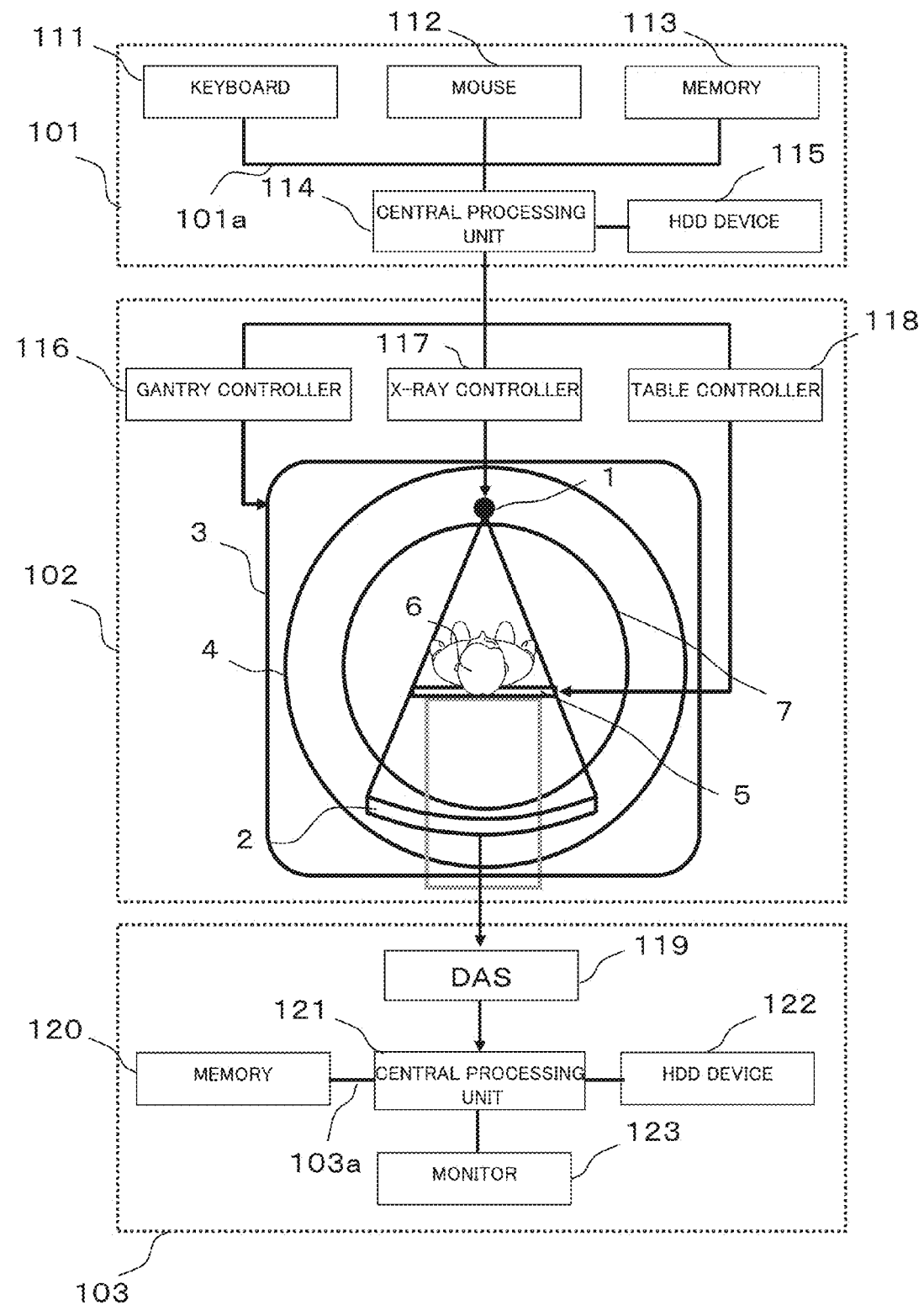
FIG. 1 is a block diagram illustrating a hardware configuration of each element of the X-ray CT apparatus in the first embodiment.

The X-ray CT apparatus of the present invention incorporates an X-ray generator configured to generate X-rays, an X-ray detector configured to detect the X-rays after passing through a subject and obtain measured projection data, a rotating plate configured to mount the X-ray generator and the X-ray detector thereon, and rotate around the subject, a local measured projection data extractor, and a second iterative approximate reconstructor. The local measured projection data extractor reconstructs the first CT image relating to a first reconstruction range of the subject, from the measured projection data obtained by the X-ray detector, and uses the first CT image to extract from the measured projection data, local measured projection data in association with the second reconstruction range within the first reconstruction range. The second iterative approximate reconstructor reconstructs the second CT image relating to a second reconstruction range, from the local measured projection data, and iteratively corrects the second CT image, so that the local calculated projection data obtained by subjecting the second CT image to the forward projection by calculation, becomes equal to the local measured projection data extracted by the local measured projection data extractor. The local measured projection data extractor is provided with a first iterative approximate reconstructor configured to iteratively correct the first CT image, so that the calculated projection data obtained by subjecting the first CT image to the forward projection by calculation becomes equal to the measured projection data detected by the X-ray detector, and uses the first CT image iteratively corrected so as to extract the local measured projection data in association with the second reconstruction range. With this configuration, it is possible to obtain the local measured projection data with a high degree of precision, thereby improving the precision of the second CT image.

The local measured projection data extractor may incorporate a background image generator configured to generate a background image that is obtained by eliminating pixels of the second reconstruction range from the first CT image that is iteratively corrected by the first iterative approximate reconstructor, a background image forward projector configured to subject the background image to the forward projection to obtain background projection data, and a subtractor configured to subtract the background projection data from the measured projection data detected by the X-ray detector to obtain the local measured projection data.

By way of example, the local measured projection data extractor may be provided with a first weight selector configured to select a weight to be used for performing iterative correction on the first CT image, and the second iterative approximate reconstructor may be provided with a second weight selector configured to select a weight to be used for the iterative correction on the second CT image. In this case, each of the first weight selector and the second weight selector may select either one of the followings; a statistical value weight and a constant value weight. The statistical value weight being variable weights to be given to output data from plural detection elements constituting the X-ray detector, in response to magnitude of the output. The constant value weight is an identical weight to be given to the output data from the plural detection elements.

The X-ray CT apparatus may further be provided with an input part configured to accept designation of the weight from an operator. In this case, each of the first weight selector and the second weight selector may be configured in such a manner as to select either one of the statistical value weight and the constant value weight, in response to the designation accepted by the input part.

It is possible to configure such that when the input part accepts from the operator, an instruction to place priority to reducing the streak artifact, the first and the second weight selectors select the statistical value weight, whereas when the input part accepts from the operator, an instruction to place priority to CT value precision, the constant value weight is selected.

It is further possible that either of the first weight selector and the second weight selector selects the statistical value weight, and the other selector selects the constant value weight.

At least one of the first and the second iterative approximate reconstructors may be configured in such a manner as to perform the iterative correction twice with switching a type of the weight. It is desirable that the first iterative correction uses the statistical value weight, the second iterative correction uses the constant value weight, and an update count of the first iterative correction is set to be larger than the update count of the second iterative correction. With this configuration, both the streak artifact and the beam hardening effect may be reduced.

The input part may be configured to accept from the operator, a designation to perform the iterative correction with switching the type of the weight. With this configuration, the first and the second iterative approximate reconstructors are allowed to perform the iterative correction twice, when the input part accepts the designation to perform the iterative correction with switching the type of the weight.

The local measured projection data extractor may further be provided with a correction necessity determination part configured to determine whether or not the iterative correction is necessary, according to the first CT image that is reconstructed from the measured projection data obtained by the X-ray detector. When the correction necessity determination part determines that the iterative correction is necessary, the first iterative approximate reconstructor is allowed to perform the iterative correction on the first CT image, and therefore this may reduce the calculation amount.

The correction necessity determination part may search an incomplete acquisition region for existence of any structural object, the incomplete acquisition region being outside a complete acquisition region of the first CT image that is reconstructed from the measured projection data obtained by the X-ray detector, and on the basis of a result of the searching, it is determined whether the correction is necessary.

In addition, the correction necessity determination part may determine whether or not the correction is necessary, depending on an output value from the detection element on the edge of the X-ray detector.

In addition, a third iterative approximate reconstructor may be provided. The third iterative approximate reconstructor may reconstruct the first CT image relating to the first reconstruction range of the subject, from the measured projection data obtained by the X-ray detector, and apply the iterative correction to the first CT image, so that the calculated projection data obtained by subjecting the first CT image to the forward projection by calculation, becomes equal to the measured projection data detected by the X-ray detector. The third iterative approximate reconstructor has a configuration that the iterative correction is performed twice with switching the type of the weight. It is desirable that the first iterative correction uses the statistical value weight being variable weight to be given to the output data from plural detection elements, in response to magnitude of the output from the plural detection elements constituting the X-ray detector, the second iterative correction uses the constant value weight being an identical weight to be given to the output data from the plural detection elements, and the update count of the first iterative correction is set to be larger than the update count of the second iterative correction.

The X-ray CT apparatus according to the second aspect of the present invention is provided with an X-ray generator configured to generate X-rays, an X-ray detector configured to detect the X-rays after passing through the subject and obtain the measured projection data, a rotating plate configured to mount the X-ray generator and the X-ray detector and rotate around the subject, and an iterative approximate reconstructor. The iterative approximate reconstructor reconstructs a CT image relating to a predetermined reconstruction range (FOV) of the subject, from the measured projection data obtained by the X-ray detector, and performs the iterative correction on the CT image in such a manner that the calculated projection data obtained by subjecting the CT image to the forward projection by calculation, becomes equal to the measured projection data obtained by the X-ray detector. At this time, the iterative approximate reconstructor is configured to perform the iterative correction twice with switching the type of the weight.

It is preferable that the iterative approximate reconstructor uses the statistical value weight in the first iterative correction out of the twice iterative corrections, the statistical value weight being variable weights to be given to the output data from the plural detection elements, in response to the magnitude of the output from the plural detection elements constituting the X-ray detector. It is desirable that the constant value weight is used in the second iterative correction, the constant weight value being an identical weight to be given to the output data from the plural detection elements, and the update count of the first iterative correction is set to be larger than the update count of the second iterative correction.

According to the third aspect of the present invention, a method of processing an X-ray CT image is provided, the method reconstructing the first CT image of the first reconstruction range from the projection data of the subject, the projection data being measured by the X-ray detector of the X-ray CT apparatus, using the first CT image to extract local measured projection data in association with the second reconstruction range within the first reconstruction range, from the projection data being measured, and generating the second CT image relating to the second reconstruction range, from the local measured projection data. At this time, the method iteratively corrects the first CT image so that the first calculated projection data obtained from the first CT image according to projection calculation becomes equal to the projection data of the subject, and uses the first CT image after the iterative correction is applied, so as to extract the local measured projection data in association with the second reconstruction range. The method iteratively corrects the second CT image, so that the extracted local measured projection data becomes equal to the second CT image.

<First Embodiment>

With reference to the accompanying drawings, the X-ray CT apparatus of the first embodiment will be explained specifically.

FIG. 1 illustrates a hardware configuration of the X-ray CT apparatus installing software for the iterative approximate reconstruction according to the first embodiment. The apparatus illustrated in FIG. 1 incorporates the input part 101 configured to input an imaging condition such as an X-ray irradiating condition and a condition for image reconstruction, an imager 102 configured to control imaging and perform X-ray irradiation and detection, and an image generator 103 configured to apply correction on the detected signals and perform image reconstruction, and output an image. It is to be noted that the input part 101 and the image generator 103 are not necessarily configured integrally with the main unit that is provided with the imager 102, and they may be placed at a distance from the imager 102 and connected thereto via a network. The input part 101 and the image generator 103 may share the hardware such as an input-output part, a processor, a storage, and the like, implementing the configurations of as those elements.

The input part 101 is provided with a keyboard 111 and a mouse 112 for inputting the imaging condition, and the like. Though not illustrated, another input means may be provided, such as a pen tablet and a touch panel. The input part 101 is provided with a CPU (Central Processing Unit) 114, a storage such as a memory 113 and HDD (Hard Disk Drive) device 115, and a monitor, not illustrated. Each of those constitutional elements are connected via a data bus 101a. The data inputted via the keyboard 111, or the like, is transferred to the CPU 114 being a processor. The CPU 114 expands and starts a predetermined program that is stored in advance, in the memory 113, the HDD device 115, and the like, thereby transferring control signals to the imager 102, and then controlling the imaging.

The imager 102 in FIG. 1 incorporates a gantry 3, a table 5 for supporting a subject 6, an X-ray controller 117, a gantry controller 116, and a table controller 118. The gantry 3 incorporates an X-ray tube 1, an X-ray detector 2, and a rotating plate 4 that mounts those elements. A circular-shaped opening 7 is provided at the center of the gantry 3 and the rotating plate 4, and the table 5 is inserted into the opening 7.

The X-ray tube 1 and the X-ray detector 2 respectively implement irradiation and detection of X-rays. A representative example of the distance between the X-ray originating point of the X-ray tube 1 and the X-ray input plane of the X-ray detector 2 is 1,000 [mm]. A representative example of the diameter of the opening 7 is 700 [mm]. A representative example of the required time per rotation of the rotating plate 4 is 1.0 [s]. A publicly known X-ray detector made up of scintillator, photo diode, and the like, is used for the X-ray detector 2. The X-ray detector 2 has many detection elements, not illustrated, being arranged along a circular arc (channel direction) at an equal distance from the X-ray tube 1, and a representative example of the number of the elements (hereinafter, referred to as "channel count") is 950. A representative example of the size of the detection element in the channel direction is 1 [mm]. The X-ray detector elements are also arranged in plural lines in the slice direction (the body-axis direction of the subject 6). The imaging count by the imager 102 per rotation of the rotating plate 4 is 900, and one imaging is performed every time the rotating plate 4 turns by 0.4 degrees. It is to be noted that the specifications are not limited to the values above, and they may be changed variously, depending on the configuration of the X-ray CT apparatus.

The gantry controller 116 controls rotating operation of the rotating plate 4. The X-ray controller 117 controls the operation of the X-ray tube 1. The table controller 118 controls the position of the table 5.

The image generator 103 incorporates a DAS (Data Acquisition System) 119, a central processing unit (CPU) 121, a storage such as the memory 120 and the HDD device 122, and the monitor 123. These elements are connected via the data bus 103a.

Signals detected by the X-ray detector 2 of the imager 102 are converted into digital signals by the DAS 119, and transferred to the CPU 121. The CPU 121 expands and starts a predetermined program stored in advance in the memory 120 and the HDD device 122, thereby applying correction and performing image reconstruction. In addition, the data is stored in the HDD device 122 and the like, and it is inputted from and outputted to the outside as appropriate. A monitor 123 being a display part, such as a liquid-crystal display and a CRT, displays the reconstructed CT image. As described above, the CPU 121, the memory 120, the monitor 123, and the like, may be shared with the input part 101.

Figure 2:
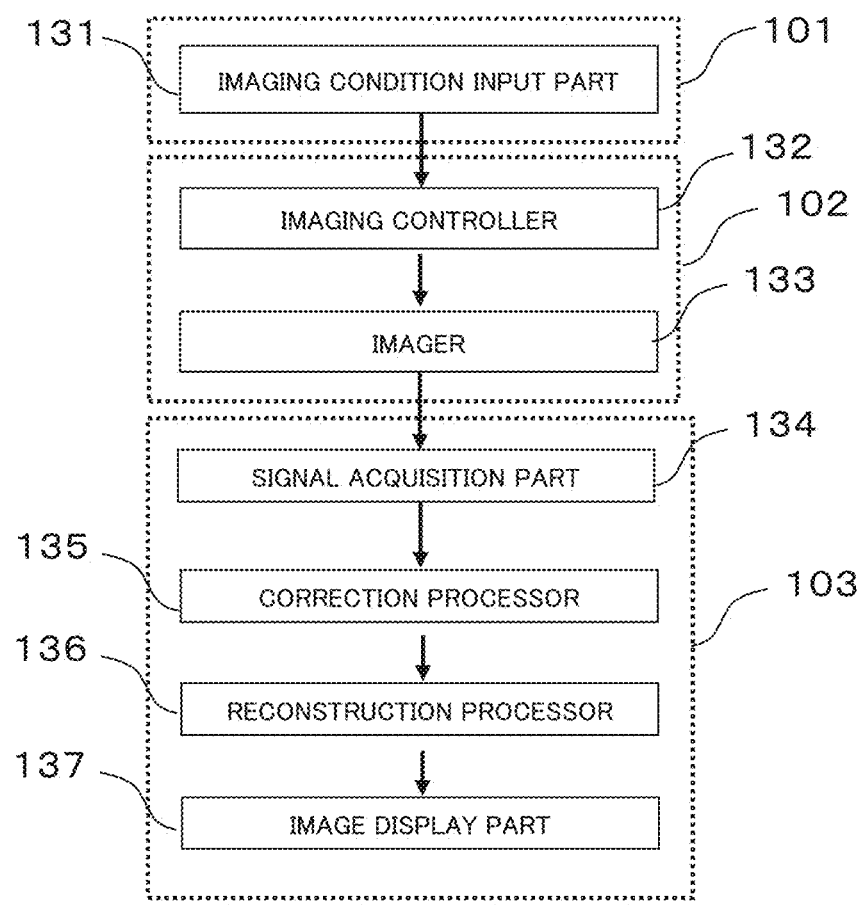
FIG. 2 is a functional block diagram of the X-ray CT apparatus in the first embodiment.

FIG. 2 is a functional block diagram of the X-ray CT apparatus according to the first embodiment. The input part 101 in FIG. 2 functions as the imaging condition input part 131 for inputting the imaging condition. The imager 102 functions as the imaging controller 132 configured to control the imaging on the basis of the imaging condition inputted through the imaging condition input part 131, and an imaging part 133 configured to perform irradiation and detection of X-rays. The image generator 103 functions as a signal acquisition part 134 configured to convert the detected signals into digital signals, a correction processor 135 configured to apply correction to the digital signals, a reconstruction processor 136 configured to perform image reconstruction on the projection data being corrected, and an image display part 137 configured to output the reconstructed CT image.

Figure 3:
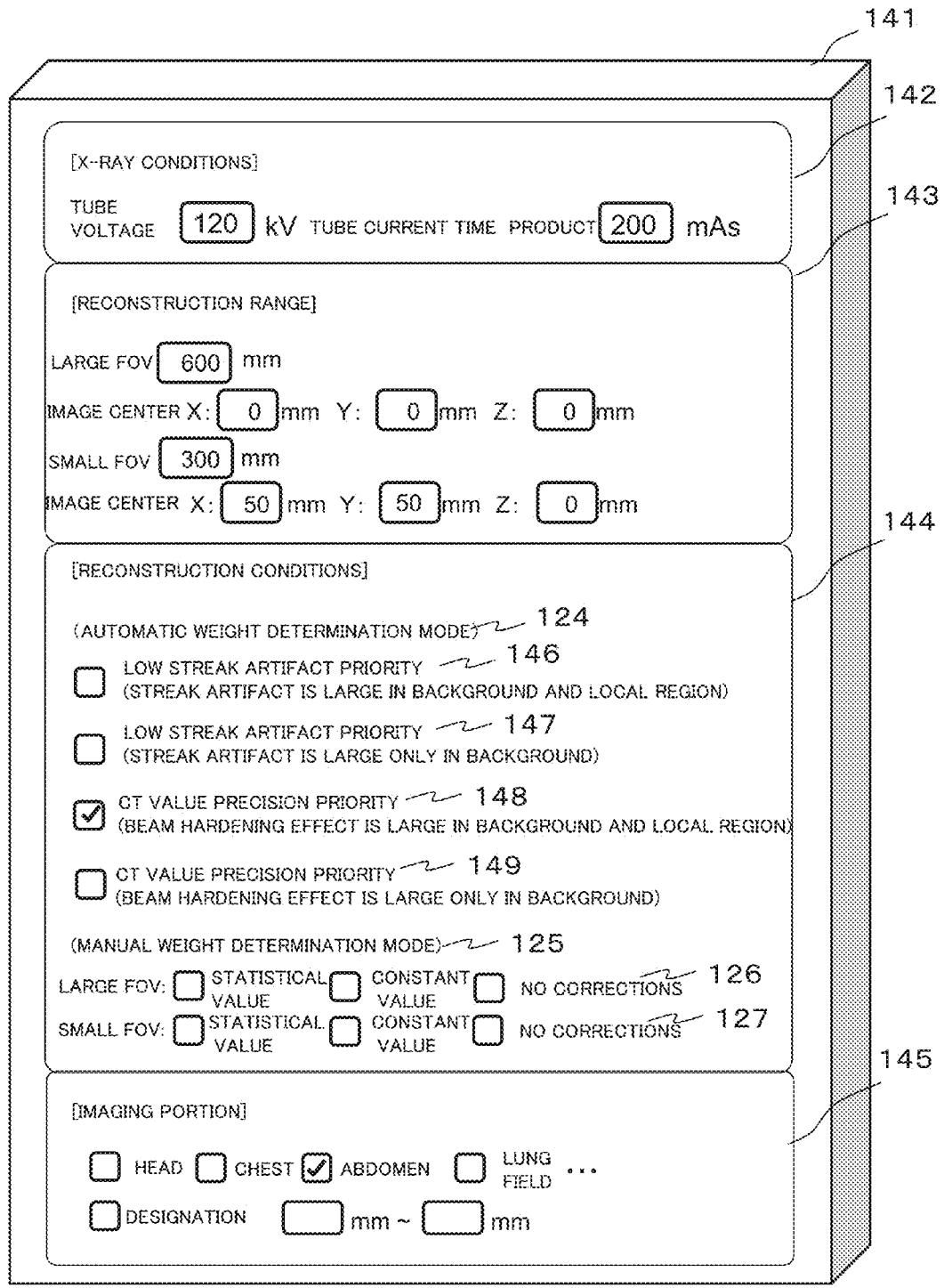
FIG. 3 illustrates an input screen of the imaging condition input part in the first embodiment.

Next, with reference to FIG. 1 to FIG. 3, an explanation will be provided as to a flow of the imaging operation of the X-ray CT apparatus according to the first embodiment. FIG. 3 illustrates one example of the imaging condition accepting screen 141 that is displayed on the monitor 123 of the imaging condition input part 131.

The imaging condition input part 131 in FIG. 2 displays the imaging condition accepting screen 141 on the monitor 123 and accepts an input from an operator. The imaging condition accepting screen 141 of FIG. 3 is made up of an X-ray condition setting area 142 configured to set tube voltage in association with the energy and output quantity of irradiated X-rays, and tube current time product, a reconstruction range setting area 143 configured to set a range of the reconstructed image, a reconstruction condition setting area 144 configured to select a weight to be used in the iterative approximate reconstruction, and an imaging portion setting area 145 configured to set an imaging portion. The operator manipulates the mouse 112, the keyboard 111, and the like, to set the X-ray condition, the reconstruction range, the reconstruction condition, the imaging portion, and the like, while viewing the imaging condition accepting screen 141. Hereinafter, more specific explanations will be provided.

In FIG. 3, as one example of the X-ray condition setting area 142, the tube voltage value is set to be 120 [kV] and the current time product is set to be 200 [mAs]. In the present embodiment, it is assumed to use the X-ray having one kind of energy spectrum. In the case of multi-energy CT using two or more kinds of X-rays, similar settings are possible by providing additional items for the tube voltage and current time product.

In the reconstruction range setting area 143 in FIG. 3, the operator sets two reconstruction ranges (FOV). The first reconstruction range (FOV) is an area to be reconstructed (hereinafter, referred to as "large FOV") 200 (see FIG. 11(a)). The second reconstruction range (FOV) is a local region within the large FOV (referred to as "small FOV") 212 to be subjected to extensive reconstruction. The size and the center position are set as to each of the large FOV 200 and the small FOV 212. The FOV in the present embodiment is defined by the shape of square. In the example of FIG. 3, the large FOV is 600 [mm] on a side and the small FOV is 300 [mm] on a side; the center position of the large FOV 200 is set to be X=Y=Z=0 [mm], which corresponds to the rotation center. The center position of the small FOV is set to be X=50 [mm], Y=50 [mm], and Z=0 [mm], that position being distant from the rotation center. It is to be noted that the large FOV 200 and the small FOV 212 are not limited to the shape of square, and it may be any shape such as a circle, a rectangle, a cube, a rectangular parallelepiped, a sphere. The present invention is applicable to any of those shapes.

The reconstruction condition setting area 144 is an area for selecting a weight to be used in the iterative approximate reconstruction that will be described below. Since this area is not used in the first embodiment, it is not explained here. It will be explained in the second embodiment. In the first embodiment, a predetermined weight is used and selection of weight is not performed here.

The imaging portion setting area 145 in FIG. 3, a target for the X-ray irradiation or a target for reconstruction is selected. A portion to be selected may not be limited to the abdomen that is selected in the present embodiment, but the portion such as the head, the chest, the lung field, or tissue may be selected, or the operator may directly designate the range.

The screen configuration of the imaging condition accepting screen 141 is not limited to the configuration as shown in FIG. 3. It is further possible to store in the HDD device 115 in advance, the settings accepted by the imaging condition accepting screen 141, including the X-ray condition, the reconstruction range, the reconstruction condition, and the portion to be imaged. In this case, it is not necessary for the operator to input the settings every time, and the imaging condition input part 131 is only required to read the settings from the HDD device 115.

Next, the imager 102 in FIG. 2 performs X-ray imaging, according to the imaging conditions accepted by the imaging condition input part 131. When the operator instructs to start imaging via the mouse 112, the keyboard 111, or the like, the imaging controller 132 within the imager 102 instructs the table controller 118 to start imaging, upon receipt of this instruction to start the imaging. The table controller 118 controls the table 5 in such a manner as to move the table in the rotation axis direction of the rotating plate 4. Then, when the position of the subject 6 coincides with the imaging position being designated, the table controller halts the movement of the table 5. Then, placing of the subject 6 is completed.

On the other hand, the imaging controller 132 instructs the gantry controller 116 to start imaging. The gantry controller 116 starts rotation of the rotation plate 4 via the drive motor, simultaneously with receiving the instruction to start imaging. At the time when the rotation of the rotating plate 4 goes into constant state, and placing the subject 6 at the imaging position is completed, the imaging controller 132 gives instructions to the X-ray controller 117, as to the X-ray irradiation timing from the X-ray tube 1 of the imager 102 and the timing of imaging by the X-ray detector 2. According to this instruction, the X-ray controller 117 causes the X-ray tube 1 to emit X-rays, and the X-ray detector 2 detects the X-rays and starts imaging. The X-ray controller 117 determines the energy spectrum and output quantity of the irradiated X-rays, on the basis of the tube voltage and the current time product of the X-ray tube 1, being set by the operator, for instance.

In the present embodiment, X-rays having only one kind of energy spectrum are used. The present embodiment is also applicable to the multi-energy CT that emits X-rays having two or more kinds of energy spectrum by switching at high speed, the tube voltage per rotation or during one rotation, and obtains imaging data.

The signal acquisition part 134 in FIG. 2 converts the output signal from the X-ray detector 2 into digital signal by the DAS 119, and stores the digital signal in the memory 120. The correction processor 135 subjects the data to corrections such as offset correction for calibrating zero value of the detected signal of X-rays, reference correction for correcting variation of signal components detected at every projection angle, and a publicly known air calibration process for correcting the sensitivity between the detection elements, and acquires measured projection data of the subject 6. The measured projection data acquired by the signal acquisition part 134 and the correction processor 135 is transferred to the reconstruction processor 136.

FIG. 4 illustrates a more detailed functional configuration of the reconstruction processor 136. The reconstruction processor 136 is provided with a local measured projection data extractor 153, and the second iterative approximate reconstructor 155 configured to iteratively reconstruct the small FOV image. The local measured projection data extractor 153 reconstructs the first CT image (large FOV image) relating to the large FOV 210 of the subject 6, from the measured projection data acquired by the signal acquisition part 134 and the correction processor 135, and extracts from the measured projection data, local measured projection data associated with the small FOV 212 on the basis of the first CT image. The way of extraction will be described in detail later. In this case here, the local measured projection data extractor 153 is provided with the first iterative approximate reconstructor 152 configured to perform iterative approximate reconstruction, when the first CT image relating to the large FOV is reconstructed. Specifically, the first iterative approximate reconstructor 152 applies the iterative correction to the first CT image, in such a manner that the calculated projection data obtained by subjecting the first CT image to forward projection by calculation becomes equal to the measured projection data. The local measured projection data extractor 153 extracts the local measured projection data associated with the small FOV 212, on the basis of the first CT image after the iterative correction is applied.

The second iterative approximate reconstructor 155 reconstructs the second CT image (small FOV image) relating to the small FOV, from the local measured projection data extracted by the local measured projection data extractor 153, and iteratively corrects the second CT image, in such a manner that the local calculated projection data obtained by subjecting the second CT image to forward projection by calculation becomes equal to the local measured projection data.

As described above, since the local measured projection data extractor 153 is able to generate the first CT image relating to the large FOV with a high degree of precision by the iterative approximate reconstruction, so as to extract the local measured projection data, it is possible to extract from the highly precise first CT image, the local measured projection data in association with the small FOV with a high degree of precision. Therefore, it is possible to generate a highly precise second CT image by the iterative reconstruction, from the local measured projection data with a high degree of precision.

Figure 5:
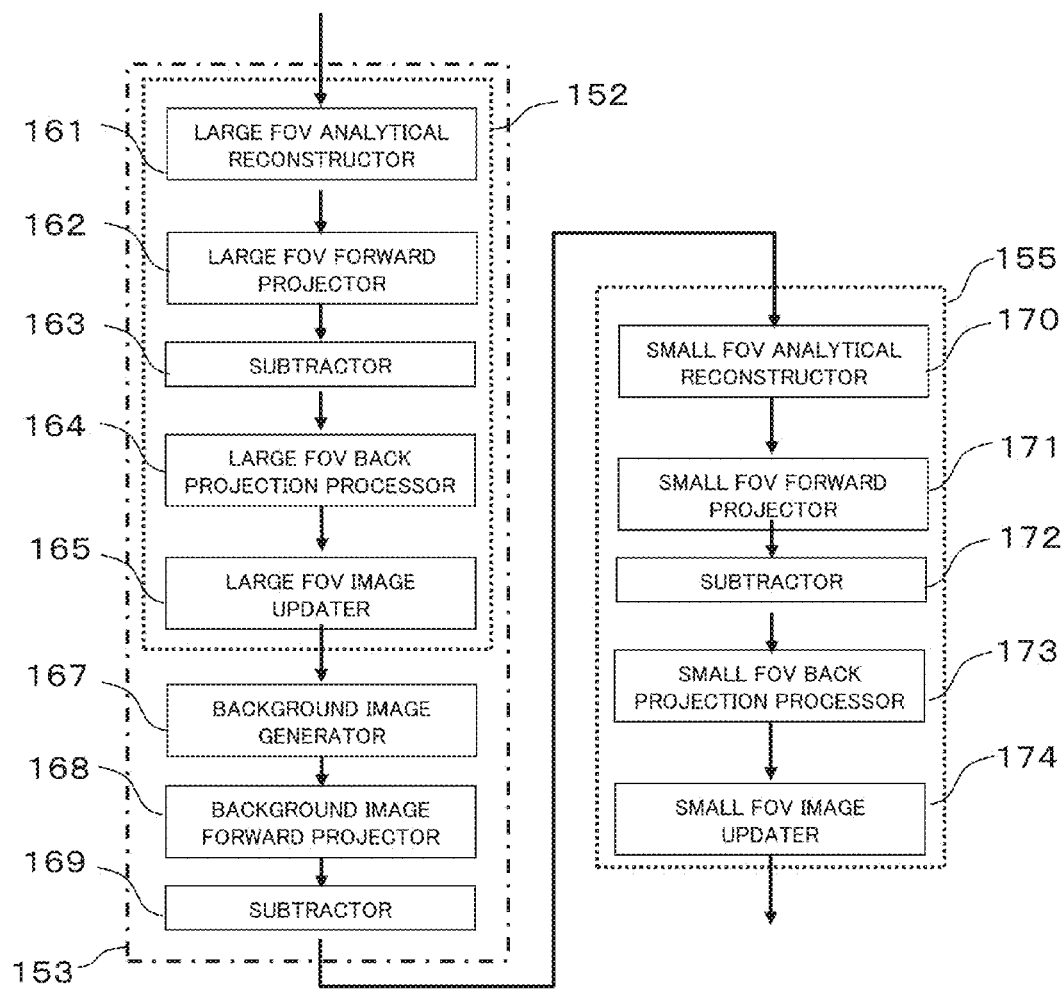
FIG. 5 is a functional block diagram illustrating the functions of the reconstruction processor 136 in the first embodiment.

Next, by using the functional block diagram in FIG. 5, an explanation will be provided as to the detailed functional configuration of the local measured projection data extractor 153 including the first iterative approximate reconstructor 152, and the second iterative approximate reconstructor 155. As shown in FIG. 5, the first iterative approximate reconstructor 152 incorporates a large FOV analytical reconstructor 161, a large FOV forward projector 162, a subtractor (data comparator) 163, a large FOV back projection processor 164, and a large FOV image updater 165. The local measured projection data extractor 153 is provided with a background image generator 167, a background image projector 168, and a subtractor (data comparator) 169, in addition to the first iterative approximate reconstructor 152. The second iterative approximate reconstructor 155 incorporates a small FOV analytical reconstructor 170, a small FOV forward projector 171, a subtractor (data comparator) 172, a small FOV back projection processor 173, and a small FOV image updater 174.

Figure 6:
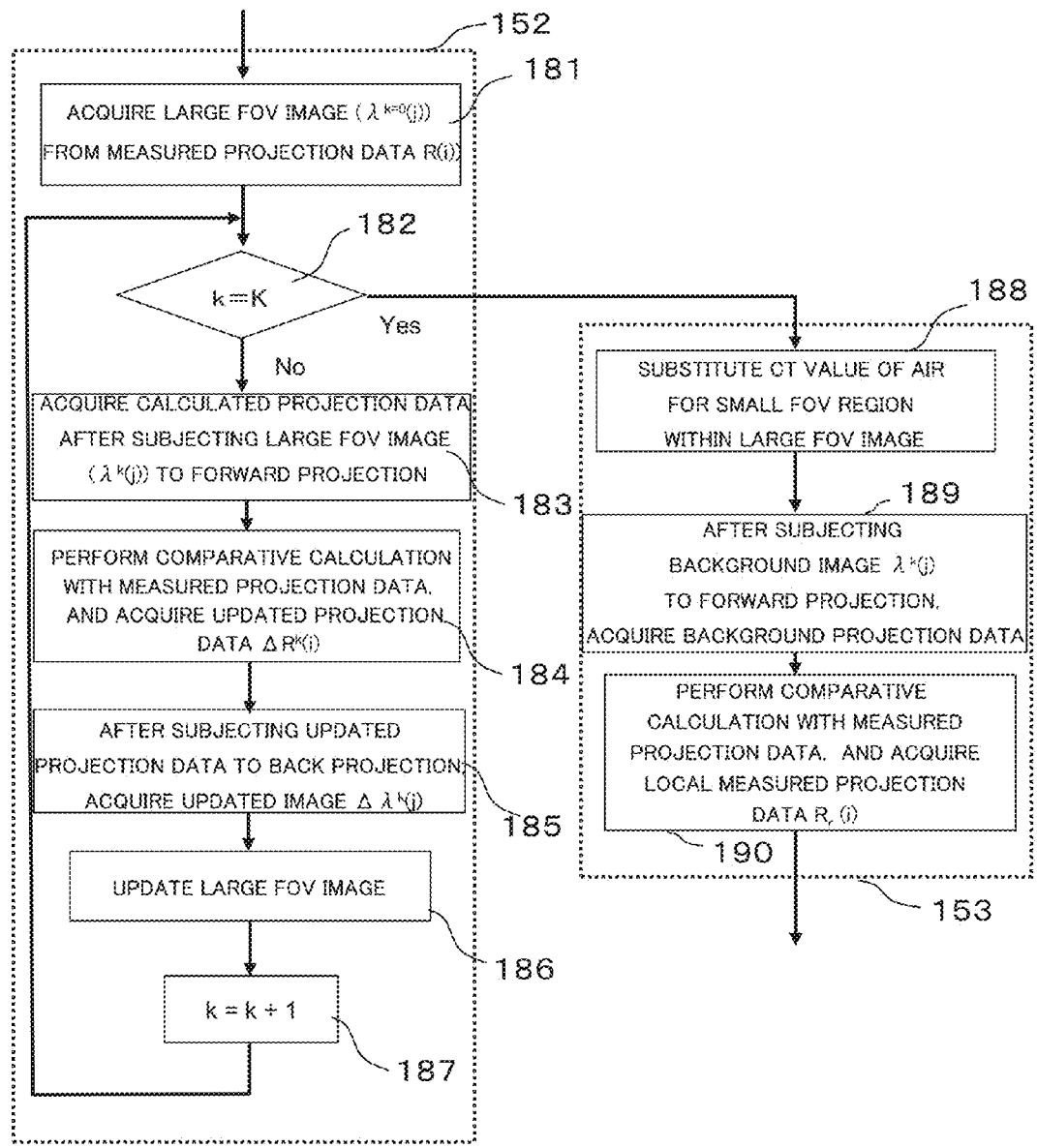
FIG. 6 is a flowchart illustrating a calculation procedure of the iterative approximate reconstruction method in the first embodiment.
Figure 7:
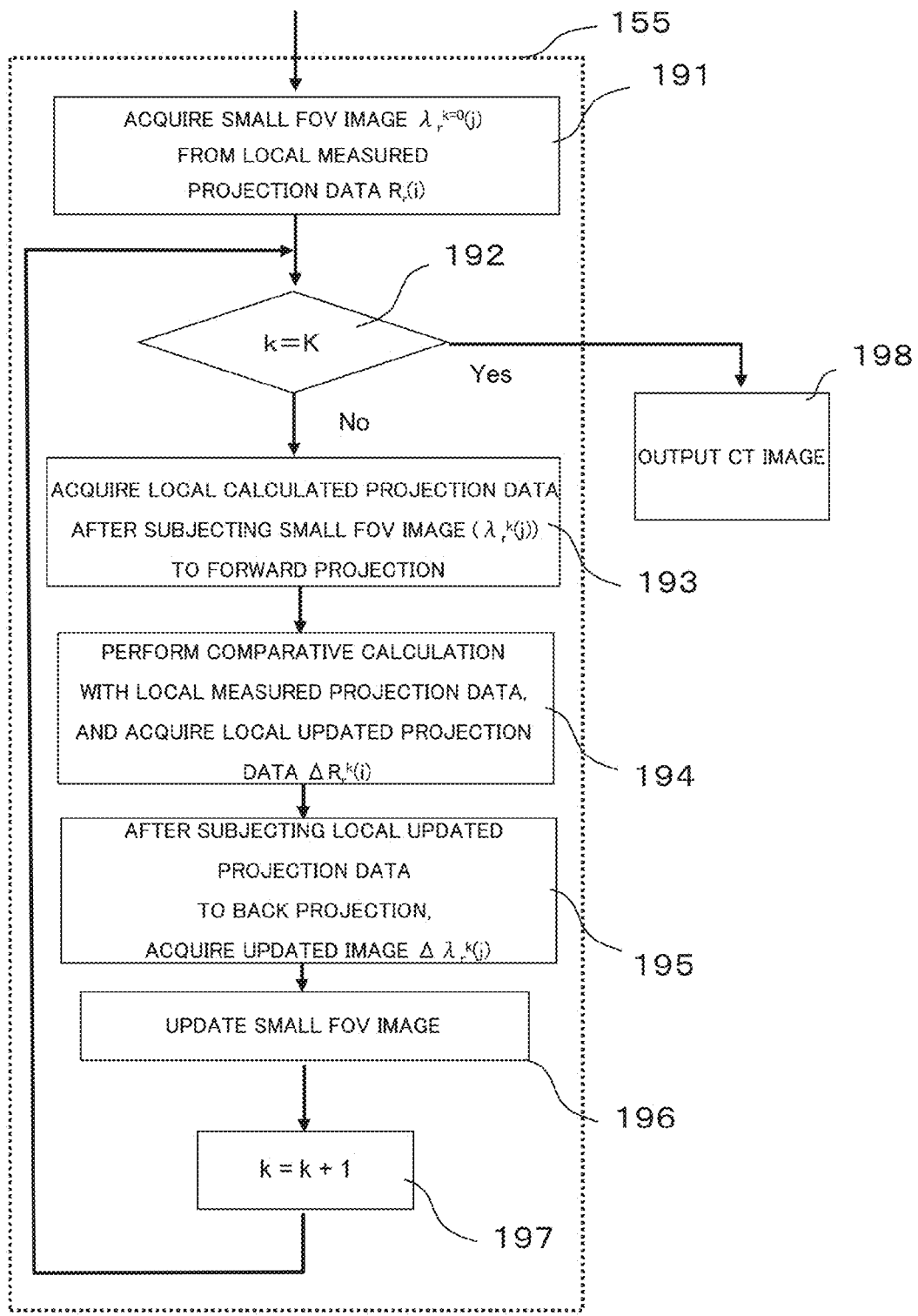
FIG. 7 is a flowchart illustrating a calculation procedure of the iterative approximate reconstruction method in the first embodiment.

Each of these functional blocks operates as shown in FIG. 6 and FIG. 7, thereby extracting highly precise local measured projection data, and reconstructing a small FOV image with a high degree of precision.

The large FOV analytical reconstructor 161 as shown in FIG. 5 employs in the step 181 of FIG. 6, an analytical reconstruction method such as the Feldkamp method being publicly known, and calculates the large FOV image ($\lambda^{k=0}(j)$) representing the CT value of the subject, from the measured projection data R(i) that is corrected by the correction processor 135. Here, i and j respectively represent the detection element number of the X-ray detector 2 and the pixel number of the image, and k represents the update count of the iterative approximate reconstruction.

The large FOV image being calculated is assumed as an initial image, and it is corrected iteratively. In other words, in the step 182, if the update count k during the calculation is smaller than the update count K being predetermined, the large FOV image is corrected according to the steps 183 to 186.

As an algorithm for correcting the image, for instance, the SPS (Separable-Paraboloidal-Surrogate) is employed, being one of the iterative approximate reconstruction methods. This SPS is expressed by the formula 1.

$$\lambda^{k+1}(j) = \lambda^{k}(j) - \frac{\sum_{i=1}^{I} W(i)C(i, j)\left(R(i) - \sum_{l=1}^{L} C(i, l)\lambda^{k}(l)\right)}{\sum_{i=1}^{I} W(i)C(i, j)\sum_{l=1}^{L} C(i, l)}$$ [Formula 1]

In the formula 1, it is assumed that $\lambda^{k}(j)$ represents a pixel value of the pixel j of the large FOV image at the update count k during the calculation, and the image is made up of J pixels. W(i) represents a weight indicating a ratio of the image correction, and it is a predetermined value. The large FOV image may be applicable not only to a tomographic image being a general two-dimensional (x and y directions), but also to one-dimensional data (x-direction), three-dimensional data (x, y, and z directions) obtained by superimposing the images in the body-axis direction z, or four-dimensional data (x, y, z, and t) considering the time direction t into the three-dimensions. Hereinafter, specific explanations will be provided.

The large FOV forward projector 162 performs the calculation of the formula 2 in the step 183, thereby subjecting the pixels in the large FOV image ($\lambda^{k}(j)$) to the forward projection process, and acquiring the calculated projection data. In the case where there are L pixels on the line connecting the pixel j of the update target with the X-ray detector i, l represents the pixel number indicating each of those pixels. Here, C(i, 1) represents the ratio of the pixel 1 contributing to the X-ray detector i, and it is changed variously, depending on the position of the X-ray detector, and a method of forward projection or a method of back projection.

$$\sum_{l=1}^{L} C(i, l)\lambda^{k}(l)$$ [Formula 2]

Next, in the step 184, the subtractor 163 subtracts the calculated projection data of the formula 2, from the measured projection data R(i), as shown in the formula 3, and obtains the update projection data $\Delta R^{k}(i)$.

$$\Delta R^{k}(i) = R(i) - \sum_{l=1}^{L} C(i, l)\lambda^{k}(l)$$ [Formula 3]

Next, the large FOV back projection processor 164 subjects the update projection data to the back projection process as shown in the formula 4 in the step 185, and acquires the update image $\Delta \lambda^{k}(j)$. Here, W(i) indicates a weight representing the ratio of the image correction.

$$\Delta \lambda^{k}(j) = \frac{\sum_{i=1}^{I} W(i)C(i, j)\Delta R^{k}(i)}{\sum_{i=1}^{I} W(i)C(i, j)\sum_{l=1}^{L} C(i, l)}$$ [Formula 4]

Next, the large FOV image updater 165 calculates the formula 5 in the step 185, thereby obtaining the large FOV image ($\lambda^{k+1}(j)$) that is corrected by using the update image.

$$\lambda^{k+1}(j) = \lambda^{k}(j) - \Delta \lambda^{k}(j)$$ [Formula 5]

As described above, after completing the steps 183 to 186, the update count k is incremented to "k+1" in the step 187, and the process returns to the step 182 to perform loop processing. At this time, when the update count k after the incrimination is equal to the preset update count K, updating is terminated, and the large FOV image is outputted.

As described above, since the large FOV image is generated by the iterative approximate reconstruction, it is generated in such a manner that the calculated projection data that is obtained by projecting the large FOV coincides with the measured projection data.

In the step 188, the background image generator 167 substitutes the CT value of the air of −1000 [HU] for the pixel values of the small FOV among the pixels in the large FOV image, the small FOV being set by the operator in the reconstruction range setting area 143 in FIG. 3. Accordingly, a background image corresponding only to a portion other than the small FOV is generated.

Next, the background image projector 168 calculates the formula 2 in the step 189, to apply the forward projection process to the background image ($\lambda^k(j)$), thereby obtaining the background projection data.

Next, the subtractor 169 calculates the formula 6 in the step 190, and subtracts the background projection data from the measured projection data R(i), thereby obtaining the local measured projection data $R_r(i)$.

$$R_r(i) = R(i) - \sum_{l=1}^{L} C(i, l)\lambda^k(l) \quad \text{[Formula 6]}$$

As described above, since the large FOV image is reconstructed according to the iterative approximate reconstruction process, its calculated projection data coincides well with the measured projection data. Therefore, the background image is generated from the large FOV image and its calculated projection data is subtracted from the measured projection data, thereby allowing the local measured projection data $R_r(i)$ in association with the small FOV to be extracted from the measured projection data, with a high degree of precision. Then, as described below, the second iterative approximate reconstructor 155 performs the iterative approximate reconstruction by using the local measured projection data $R_r(i)$, thereby generating the small FOV image with a high degree of precision.

Specifically, the small FOV analytical reconstructor 170 of the second iterative approximate reconstructor 155 calculates the small FOV image ($\lambda_r^{k=0}(j)$) from the local measured projection data $R_r(i)$ in the step 191 of FIG. 7, by the analytical reconstruction method such as the Feldkamp method being publicly known.

Next, assuming thus calculated small FOV image as an initial image of the iterative approximate reconstruction method, the image is iteratively corrected. In the step 192, when the update count k during the calculation is smaller than the preset update count K, the image is corrected by using the local measured projection data $R_r(i)$ in the steps from 193 to 196. As an algorithm for correcting the image, for instance, if the SPS being one of the iterative approximate reconstruction methods is used, the image is corrected by calculating the formula 7.

$$\lambda_r^{k+1}(j) = \lambda_r^k(j) - \frac{\sum_{i=1}^{I} W_r(i)C(i, j)\left(R_r(i) - \sum_{l=1}^{L} C(i, l)\lambda_r^k(l)\right)}{\sum_{i=1}^{I} W_r(i)C(i, j)\sum_{l=1}^{L} C(i, l)} \quad \text{[Formula 7]}$$

In the formula 7, $\lambda_r^k(j)$ represents a pixel value of the pixel j of the small FOV image at the update count k during the calculation, and it is assumed that the small FOV image is made up J pixels. Here, $W_r(i)$ indicates a weight representing the ratio of the image correction, and it is a value being predefined. The small FOV image may be applicable not only to a general two-dimensional (x and y directions) tomographic image, but also to one-dimensional data (x direction), three-dimensional data (x, y, and z directions) obtained by superimposing the images in the body-axis direction z, or a four-dimensional data (x, y, z, and t) considering the time direction t into the three-dimensions. Hereinafter, a specific explanation will be provided.

The small FOV forward projector 170 uses in the step 193, the aforementioned formula 2 in which the small FOV image ($\lambda_r^k(j)$) substitutes for the large FOV image ($\lambda^k(j)$), so as to obtain the calculated projection data of the local region (the local calculated projection data). Next, the subtractor 172 calculates in the step 194, the formula in which the small FOV image ($\lambda_r^k(j)$) substitutes for the large FOV image ($\lambda^k(j)$) in the formula 3, thereby obtaining the local update projection data $\Delta R_r^k(i)$. Next, the small FOV back projection processor 173 calculates in the step 195, the formula in which the small FOV image ($\lambda_r^k(j)$) substitutes for the large FOV image ($\lambda^k(j)$) shown in the formula 4, and applies the back projection process to the local update projection data $\Delta R_r^k(i)$, thereby acquiring the update image $\Delta_r^k(j)$. A predetermined value is used as the weight $W_r(i)$.

Next, the small FOV image updater 174 calculates in the step 196, the formula in which the small FOV image ($\lambda_r^k(j)$) substitutes for the large FOV image ($\lambda^k(j)$) in the formula 5, thereby obtaining the small FOV image $\lambda_r^{k+1}(j)$ that is corrected by using the update image.

After completing the steps from 193 to 196, the update count k is incremented to (k+1) in the step 197, and then returning to the step 192 to perform the loop processing. At this time, if the update count k after the incrimination is equal to the update count K being predefined, the update is completed, and in the step 198, the image display part 137 outputs the small FOV image (the second CT image).

In the aforementioned steps from 181 to 198, there has been described the calculation procedure of the extensive reconstruction technique in the iterative approximate reconstruction method. In the extensive reconstruction technique, the CT value precision of the small FOV image is dependent on the precision degree of the local measured projection data. In the present embodiment, in order to extract the local measured projection data, the iterative approximate reconstruction of the large FOV image is performed, and therefore, it is possible to obtain the calculated projection data of the background image, well coinciding with the measured projection data relating to the background image with a high degree of precision. Therefore, by subtracting the calculated projection data of the background image from the measured projection data, thereby extracting the local measured projection data with a high degree of precision.

The iterative approximate reconstruction method as shown in the formula 1 or formula 7 of the first embodiment is just an example, and another method may also be applicable, such as a publicly known OS-SPS, PWLS, OS-PWLS, ASIRT, MSIRT, GRADY, CONGR, ART, SART, ML-EM, OS-EM, FIRA, RAMLA, and DRAMA.

Finally, the image display part 137 displays thus calculated CT image on the monitor 123 to provide information to the operator. It is further possible to use a network adapter so as to establish connection with outside terminals, via the network such as a local area network, a telephone line, and the Internet, and transmit/receive the CT image to and from the outside terminals.

The subject explained in the present embodiment indicates an imaging target, and it includes the subject 6 and the table 5 that supports the subject 6. It is to be noted that the subject 6 may not be limited to a human body, but it may be an object being an inspection target, such as a phantom and a machine.

In the present embodiment, the local measured projection data is reconstructed, but this is not the only example. It is also possible to employ a method that reconstructs the small FOV image in the state that the background image is fixed to a pixel size of the large FOV image, and subjects both the small FOV image and the background image to the iterative correction simultaneously. In this case, it is not necessarily required to set the update count used for correcting the background image to agree with the update count used for correcting the small FOV image. Even when correction of either one is completed, the correction of the other may be continued.

In the present embodiment, the measured projection data acquired by rotation of one round is used to reconstruct the CT image, but it is not limited to one round, and the present embodiment is also applicable to a half-reconstruction being publicly known. In this case, a complete measurement field is assumed as a region at the rotation angles satisfying a complete acquisition condition in the half reconstruction.

In the present embodiment, it is assumed that a normal scanning method is employed. It is of course possible to apply the present invention to the step-and-shoot method that repeats normal scanning at a certain interval in the order of activation and halt of the table 5, and the helical scanning method that performs imaging while moving the table.

In the present embodiment, the X-ray CT apparatus used for a living body is taken as one example. It is of course possible to apply the present invention to the X-ray CT apparatus aiming at non-destructive inspections, such as a bomb test and a product inspection. Further in the present embodiment, the publicly known third-generation multi-slice X-ray CT apparatus is taken as one example. The present invention is also applicable to a publicly known first, second, or a fourth generation X-ray CT apparatus, and the present invention is also applicable to a publicly known single slice X-ray CT apparatus and an electron beam CT.

<Second Embodiment>

Next, an explanation will be provided as to the X-ray CT apparatus of the second embodiment. In the first embodiment, the first iterative approximate reconstructor 152 for performing the iterative approximate reconstruction to obtain the large FOV, has a configuration to use a predetermined value as the weight W(i) when the iterative approximate reconstruction is performed according to the formula 1. Similarly, the second iterative approximate reconstructor 155 for performing the iterative approximate reconstruction to obtain the small FOV, has a configuration to use a predetermined value as the weight $W_r(i)$ when the iterative approximate reconstruction is performed according to the formula 7. On the other hand, in the second embodiment, the weight W(i) used in the iterative approximate reconstruction for the large FOV image, or the weight $W_r(i)$ used in the iterative approximate reconstruction for the small FOV image, are set to the weight of appropriate type, in response to the type of the errors in the large FOV image or in the small FOV image, thereby restrain lowering of the CT value precision in the small FOV image.

There are two types of the weight to be used as the weight W(i) in the iterative approximate reconstruction for the large FOV image or the weight $W_r(i)$ used in the iterative approximate reconstruction for the small FOV image; constant value weight (constant number) and statistical value weight.

When the constant value weight is used as the weight W(i) or the $W_r(i)$, irrespective of the number assigned to the detection element (pixel number) i of in the X-ray detector 2, a value of the constant value weight (constant number) is set as W(i) or $W_r(i)$. Here, any magnitude of the constant value weight (constant) may produce similar effects. It is because, as obvious from the aforementioned formula 1 and formula 7, W(i) or $W_r(i)$ is included both in the numerator and denominator.

When the statistical value weight is used as the weight W(i) or $W_r(i)$, the magnitude of the weight defined according to (or in proportion to) the output signal value from the detection element with the number i of the X-ray detector 2, is set as W(i) or $W_r(i)$. In other words, when the output signal from the m-th detection element is large, a large value is set to the weight W(m), and when the output signal from the n-th detection element is small, a small value is set to the weight W(n).

Figure 10:
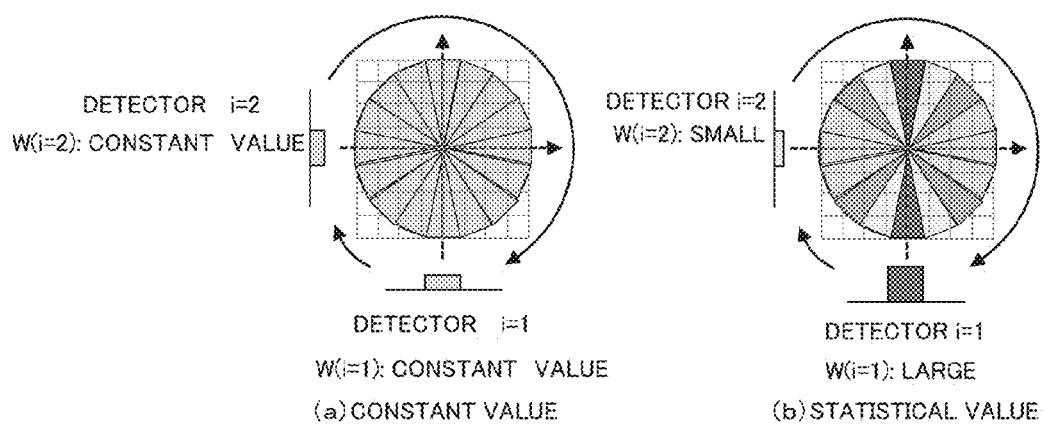
FIG. 10 illustrates types of the weight used for the correction in the second embodiment.

With reference to FIG. 10(a) and FIG. 10(b), an effect will be explained, when the constant value weight or the statistical value weight is set to the weight W(i) or $W_r(i)$. FIG. 10(a) illustrates an image obtained by giving a constant value as the weight W(i) of the center detection element i=1, i=2 . . . i=I, positioned at the center of the X-ray detector 2 at each projection angle, and performing the back projection calculation. FIG. 10(b) illustrates an image obtained by giving the statistical value weight as the weight W(i) of the center detection element i=1, i=2 . . . i=I, and performing the back projection calculation. In FIG. 10(a) and FIG. 10(b), the depth of gray color represents each pixel value (CT value). As shown in FIG. 10(a), when the constant value weight is used, it is found that the pixel value varies continuously, without depending on the projection angle. On the other hand, as shown in FIG. 10(b), when the statistical value weight is used, it is found that the pixel value varies discretely depending on the projection angle. FIG. 10(a) and FIG. 10(b) illustrates the images obtained by the back projection, relating only to the weight of the center detection element. However, it is a matter of course that as for the weight of any detection element placed in the channel direction or in the slice direction, similar operations for correcting the image may be obtained depending on the type of the weight.

As shown in FIG. 10(a), when the iterative approximate reconstruction is performed, the constant value weight is used irrespective of the number i of the detection element, and it is possible to correct the image on the basis of the update projection data of all the detection elements without depending on the projection angle. Accordingly, unevenness between the pixels due to the correction is small in the CT image, and homogeneous image quality improvement is obtained. By way of example, with the usage of the constant value weight, even when the value of the measured projection data causes a different beam hardening effect depending on the condition of the subject through which X-ray passes, it is possible to obtain the homogeneous image quality improvement without emphasizing the correction of the projection data at some projection angles. As for the errors in the incomplete reconstruction and errors in the reference correction, the constant value weight is also used, and thereby correcting the image with an equal ratio, on the basis of the update projection data at each projection angle. Therefore, it is possible to restrain lowering of the CT value precision, without emphasizing the correction at some projection angles. Using the constant value weight has the following drawbacks; since it is assumed that the noise of the measured projection data is equal throughout all the X-ray detectors, noise reduction effects may not be obtained sufficiently, unlike the case of using the statistical value weight.

On the other hand, in the iterative approximate reconstruction, the statistical value weight is used in response to the output signal magnitude from the detection element having the detection element number i, and the ratio of correction of the image is allowed to be variable, according to the noise of the projection data that is measured by the detection element. With this configuration, the image is corrected focusing on the projection data having low noise, and it is possible to effectively reduce the quantum noise, circuit noise, and streak artifact. Using the statistical value weight has the following drawbacks; for the projection data at the projection angle having a large beam hardening effect, the correction may be emphasized in response to the weight, and homogeneous quality improvement may not be expected. This may reduce the CT value precision.

In the second embodiment, the aforementioned characteristics of the constant value weight and the statistical value weight are utilized so as to set the weight of appropriate type depending on the image, thereby restraining deterioration of the CT value precision in the small FOV image.

Hereinafter, the configurations of the X-ray CT apparatus in the second embodiment being the same as those of the first embodiment may not be tediously explained, but only the different configuration will be explained.

Figure 8:
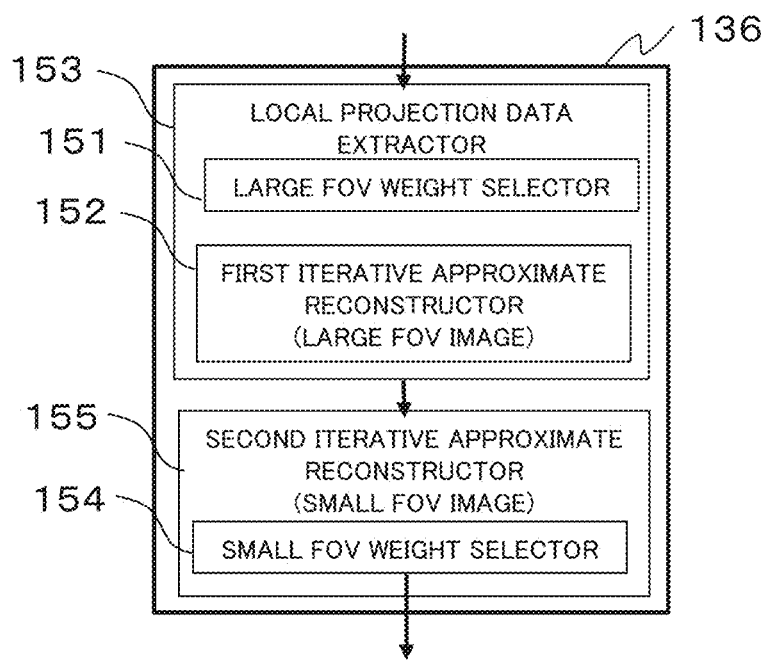
FIG. 8 is a functional block diagram illustrating the functions of the reconstruction processor 136 in the second embodiment.
Figure 9:
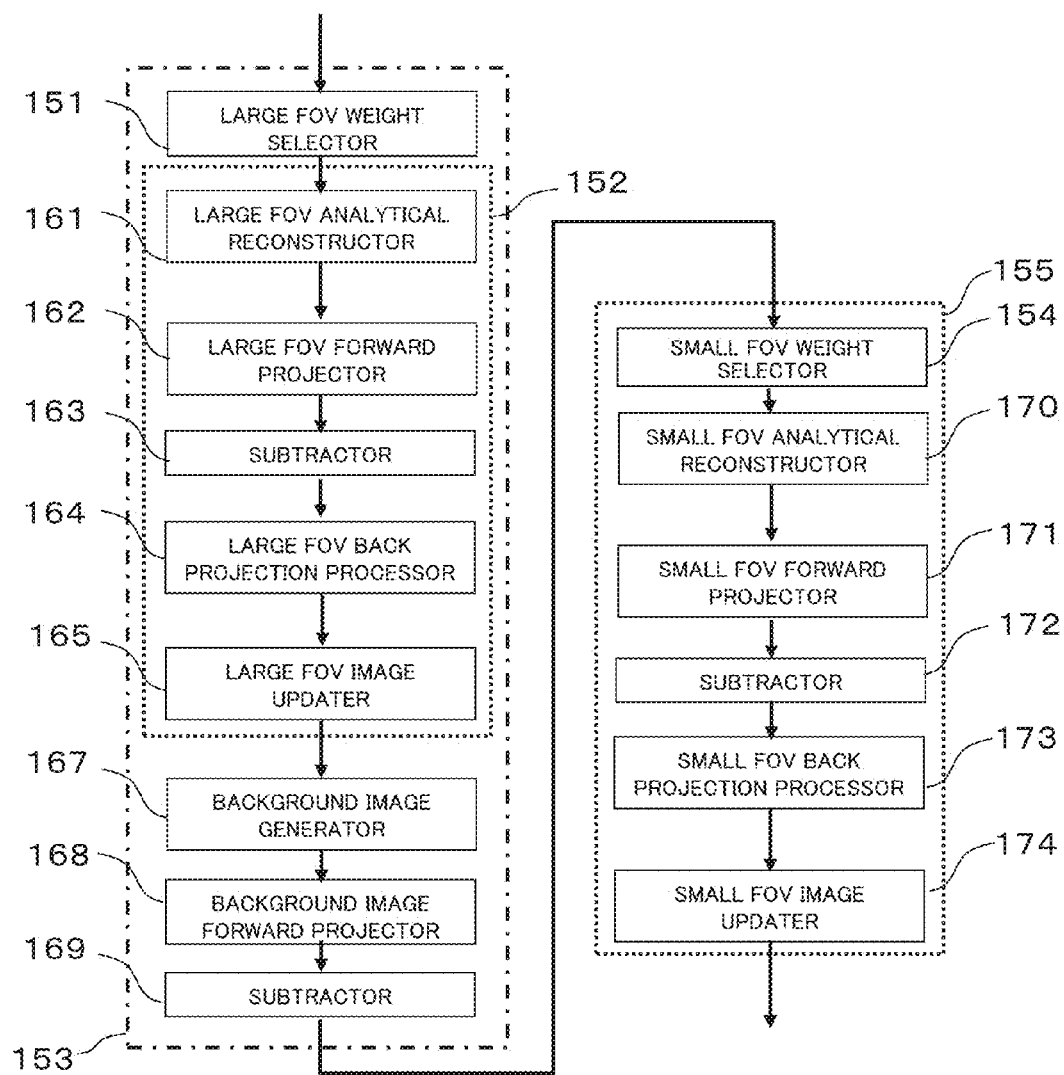
FIG. 9 is a functional block diagram illustrating the functions of the reconstruction processor 136 in the second embodiment.

As illustrated in FIG. 8 and FIG. 9, there is placed within the local measured projection data extractor 153, a large FOV weight selector 151 configured to select the weight W(i) in performing the iterative approximate reconstruction to obtain the large FOV image, and there is placed within the second iterative approximate reconstructor 155, a small FOV weight selector 154 configured to select the weight $W_r(i)$ in performing the iterative approximate reconstruction to obtain the small FOV image.

In the second embodiment, the large FOV weight selector 151 is configured prior to the analytical reconstructor 152, but the configuration is not limited to the present embodiment. It may be configured after the analytical reconstructor 152.

The imaging condition accepting screen 141 in FIG. 3 is provided with the reconstruction condition setting area 144, and it is configured such that following modes are displayed for allowing the operator to choose either of the modes; a mode 124 for automatically determining the weight W(i) and $W_r(i)$ used for the iterative approximate reconstruction of the large FOV image and the small FOV image, and a mode 125 for manually selecting the weights.

In the automatic weight determination mode 124, there are displayed two types of modes 146 and 147 in selectable manner, placing priority to reducing the streak artifact rather than other artifacts. Here, when the streak artifact is large in both in the background image that is obtained by removing the small FOV image from the large FOV image, and in the small FOV image (local region), the mode 146 is used for performing a process to reduce the streak artifact in both images. The mode 147 is used for performing a process to reduce the streak artifact in the background image, when the streak artifact is large only in the background image of the large FOV. Further in the automatic weight determination mode 124, there are also displayed two types of modes 148 and 149 for reducing beam hardening, while keeping the CT value precision. When the beam hardening effect is large both in the background image and in the small FOV image (local region), the mode 148 reduces the beam hardening effect in both images. The mode 149 is a used for reducing the beam hardening effect, when it is large only in the background image.

In the manual weight determination mode 125, there are provided the following fields for manually selecting the weight; the field 126 for selecting as the weight (i) to be used in the iterative approximate reconstruction to obtain the large FOV image, any of the statistical value weight, the constant value weight, and no corrections, and the field 127 for selecting as $W_r(i)$ to be used in the iterative approximate reconstruction to obtain the small FOV image, any of the statistical value weight, the constant value weight, and no corrections.

In the automatic weight determination mode 124, if the low streak artifact priority mode 146 (when the streak artifact in both the background and the local region is large) is selected by the operator, both of the large FOV weight selector 151 and the small FOV weight selector 154 in FIG. 8 select the statistical value weight as the weight W(i) and $W_r(i)$, and those are set in the first and the second iterative approximate reconstructors 152 and 155, respectively. With this configuration, it is possible to reduce the streak artifact, the quantum noise, and the circuit noise, effectively in the large FOV image and the small FOV image.

Next, if the operator selects the low streak artifact priority mode 147 (when the streak artifact is large only in the background), the large FOV weight selector 151 in FIG. 8 selects the statistical value weight as the weight W(i), and the small FOV weight selector 154 selects the constant value weight as the weight $W_r(i)$. With this configuration, it is possible to effectively reduce the streak artifact, the quantum noise, and the circuit noise in the background image (large FOV image), whereas in the small FOV image, it is possible to reduce the beam hardening effect, errors in the incomplete reconstruction, and errors in the reference correction. Accordingly, in the case where different errors are observed in the large FOV image and the small FOV image, such as when a large streak artifact occurs particularly in the background image of the large FOV image, it is possible to reduce such errors, thereby restraining the lowering of the CT value precision.

If the operator selects the CT value precision priority mode 148 (when the beam hardening effect in the background and the local region is large), the large FOV weight selector 151 and the small FOV weight selector 154 in FIG. 8 select the constant value weight as the weight W(i) and $W_r(i)$. With this configuration, it is possible to reduce the beam hardening effect, errors in the incomplete reconstruction, and errors in the reference correction in the large FOV image and the small FOV image.

Next, if the operator selects the CT value precision priority mode 149 (when the beam hardening effect is large only in the background), the large FOV weight selector 151 selects the constant value weight as the weight W(i), and the small FOV weight selector 154 selects the statistical value weight as the weight $W_r(i)$. With this configuration, it is possible to reduce the beam hardening effect, errors in the incomplete reconstruction, and errors in the reference correction in the background image (large FOV image), and in the small FOV image, it is possible to effectively reduce the streak artifact, the quantum noise, and the circuit noise. Accordingly, in the case where different errors are observed in the large FOV image and the small FOV image, such as when the beam hardening effect occurs particularly in the background image of the large FOV image, it is possible to reduce such errors, thereby restraining the lowering of the CT value precision.

In the manual weight determination mode 125, the large FOV weight selector 151 selects as the weight W(i), the type of weight that is manually selected in the field 126 of FIG. 3. The small FOV weight selector 154 selects as the weight $W_r(i)$, the type of weight that is manually selected in the field 127 of FIG. 3. Accordingly, any of the combinations may provide the same effects as those in the aforementioned modes 146 to 149. In any of the cases, when the option of "no corrections" is selected, the image is not corrected.

In the extensive reconstruction technique, the CT value precision of the small FOV image is dependent on the precision of the local measured projection data. As a main factor that deteriorates this precision, lowering of the CT value precision in the large FOV image is conceivable. Here, quantum noise, circuit noise, streak artifact, beam hardening effects, errors in incomplete reconstruction, and errors in reference correction are taken as the examples. As one example of the incomplete reconstruction, errors may increase in the analytical reconstruction method, when data at some projection angles is not measured in the periphery of the FOV. Errors that occur in the image of the background region may lower the precision of the local measured projection data, via the background projection data that is obtained by the forward projection calculation. Accordingly, the small FOV image is corrected by using the local measured projection data with a low degree of precision, and thus this may deteriorate the CT value precision. On the other hand, in the second embodiment, the weight W(i) and $W_r(i)$ used for correcting the large FOV image and the small FOV image, respectively, are changed in response to the type of errors in the large FOV image and the small FOV image, thereby restraining the deterioration of the CT value precision in the small FOV image.

In order to validate the utility of the second embodiment, a simulation experiment was conducted under the condition considering the quantum noise. The phantom targeted for imaging was set, assuming a human body abdomen in the elliptic shape. The phantom of the human abdomen had a structure provided with a CT value of water, being close to living tissue.

FIG. 11(a) illustrates an original image of the large FOV 200. The circle 211 as shown in FIG. 11(a) indicates a boundary between the complete acquisition region 241 within the circle, and the incomplete acquisition region 244 outside the circle. In this case, the complete acquisition region 241 indicates a region where the projection data is able to be acquired at the projection angles corresponding to one rotation, and in contrast to the complete acquisition region 241, the incomplete acquisition region 244 indicates a region where the projection data at some projection angles fail to be acquired.

FIG. 11(b) illustrates an image in association with the small FOV 212, which is obtained by the FBP method being a conventional analytical reconstruction method.

FIG. 11(c) to FIG. 11(e) show the results of simulation performed by applying the extensive reconstruction technique to the large FOV image that was reconstructed in association with the large FOV (=550 [mm]) 200 in FIG. 11(a), and subjecting the small FOV image of the small FOV (=250 [mm]) 212 to the iterative approximate reconstruction. FIG. 11(b) illustrates the initial image $\lambda_r^k=0(j)$ for the iterative approximate reconstruction of FIG. 11(c) to FIG. 11(e). FIG. 11(c) illustrates the case where the large FOV image was not corrected (no corrections on the image), and the statistical value weight was used as the weight $W_r(i)$ for correcting the small FOV image. FIG. 11(d) illustrates the case where the statistical value weight was used as both of the weights W(i) and $W_r(i)$ for correcting the large FOV image and the small FOV image. FIG. 11(e) illustrates the case where the constant value weight was used as the weight W(i) for correcting the large FOV image, and the statistical value weight was used as the weight $W_r(i)$ for correcting the small FOV image. In FIG. 11(b) to FIG. 11(e), the window level (hereinafter, referred to as "WL") was equal to −15 [HU], and the window width (hereinafter, referred to as "WW") was equal to 200 [HU]. It is to be noted that, for the iterative approximate reconstruction in FIG. 11(c) to FIG. 11(e), the simulation was performed under the conditions that the OS-SPS using a publicly known subset method was employed, the update count of the large FOV image was set to be 50 times, the update count of the small FOV image was set to be 20 times, and the number of subsets was equal to 24.

FIG. 11(f) to FIG. 11(h) illustrate the images taking the differences between each of the results of the iterative approximate reconstruction method as shown in FIG. 11(c) to FIG. 11(e), and the result of the FBP method being the conventional analytical reconstruction method as shown in FIG. 11(b). In FIG. 11(f) to FIG. 11(h), WL was equal to be 0 [HU] and WW was equal to be 100 [HU].

When the images in FIG. 11(c) to FIG. 11(h) are evaluated, the image in FIG. 11(c) where the large FOV image was not corrected (no corrections on the image), and the statistical value weight was used as the weight $W_r(i)$ for correcting the small FOV image shows lowering of the CT value precision at the points as indicated by the arrows. The image of FIG. 11(g) obtained by taking a difference between the image of FIG. 11(d) in the case where the statistical value weight was used for both of the weights W(i) and $W_r(i)$ for correcting the large FOV image and the small FOV image, and the image according to the FBP method of FIG. 11(b) shows slight lowering of the CT value precision at the points indicated by the arrows. On the other hand, the image of FIG. 11(e) shows no lowering of CT value precision, where the constant value weight was used as the weight W(i) for correcting the large FOV image, and the statistical value weight was used as the weight $W_r(i)$ for correcting the small FOV image. Similarly, the image of FIG. 11(h) obtained by taking a difference between the image of FIG. 11(e) and the image of FIG. 11(b) does not indicate any lowering of the CT value precision.

On the other hand, FIG. 11(i) illustrates a position of the circular region of interest (hereinafter, referred to as "ROI") for evaluating the images of FIG. 11(f) to FIG. 11(h). As shown in FIG. 11(i), the ROI 213 is set on the upper layer, the ROI 214 is set on the middle layer, and the ROI 215 is set on the lower layer of the image.

The graph of FIG. 11(j) is a result obtained by quantitatively measuring the CT values within the ROI 213, the ROI 214, and the ROI 215 as shown in FIG. 11(i). The difference CT value on the vertical axis indicates the CT value after the subtraction using the FBP method of FIG. 11(b), showing that as the value approaches zero, the more is restrained the lowering of the CT value precision due to the extensive reconstruction technique. According to FIG. 11(j), it is found that the image of FIG. 11(h) indicates the smallest difference CT value. Therefore, when there is any error in the original image, due to the incomplete reconstruction, it is effective to employ a method that uses the constant value weight for correcting the large FOV image, and uses the statistical value weight for correcting the small FOV image.

<Third Embodiment>

Next, as the third embodiment, an explanation will be provided as to the X-ray CT apparatus installing the iterative approximate reconstructing software, obtained by modifying a part of the first embodiment and the second embodiment.

In the X-ray CT apparatus of the third embodiment, the following point is different from the first embodiment or the second embodiment; that is, the type of the weight used for the large FOV image or for the small FOV image is changed in the middle of the iterative approximate reconstruction. Hereinafter, an explanation will be provided as to the essential portion of the X-ray CT apparatus according to the third embodiment. Beside this portion, the third embodiment has the same configurations and the operations as those of the X-ray CT apparatus explained in the first embodiment or in the second embodiment, and thus tedious explanations will not be provided.

Figure 12:
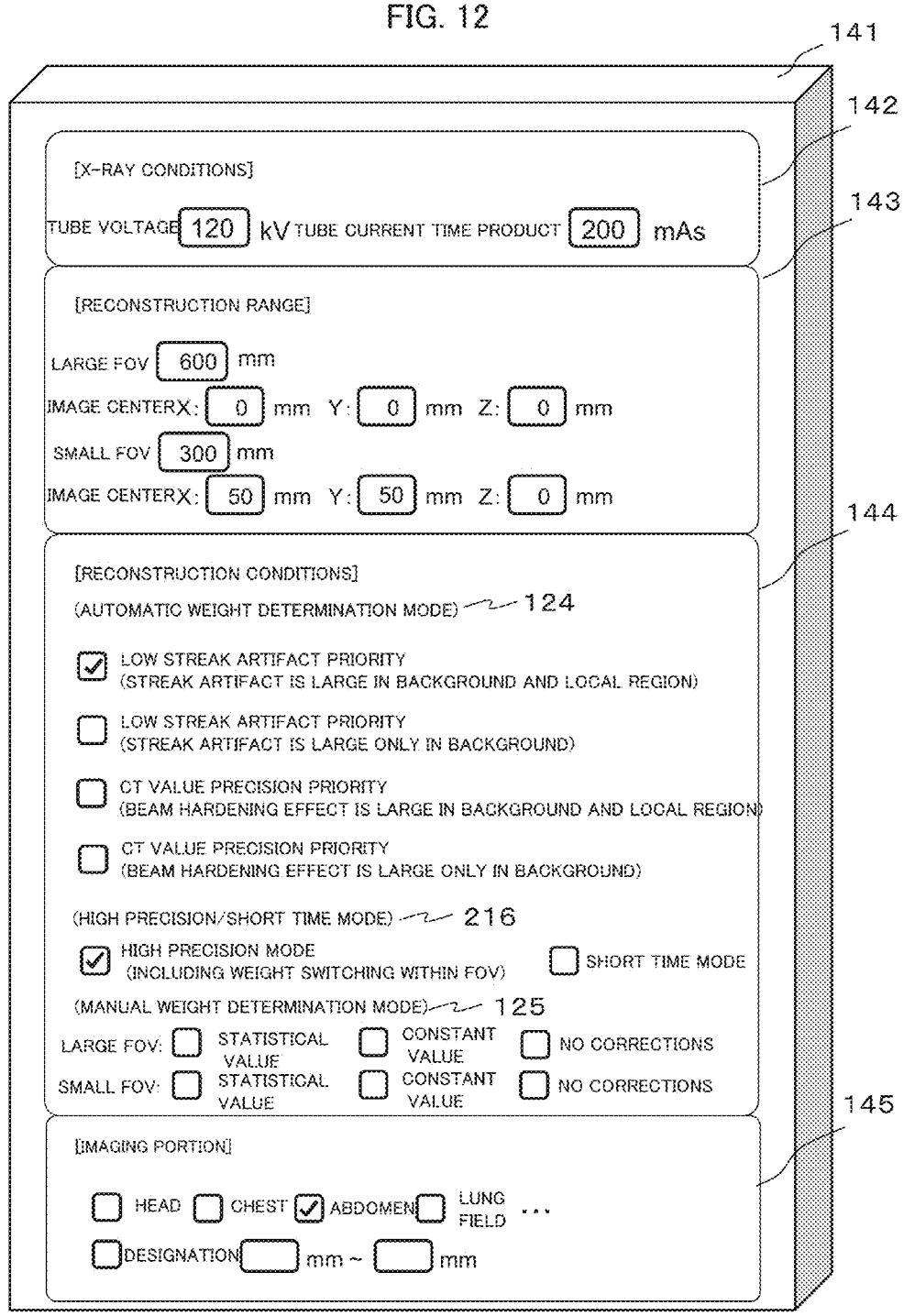
FIG. 12 illustrates the input screen of the imaging condition input part in the third embodiment.

FIG. 12 illustrates the imaging condition accepting screen 141 that is displayed on the monitor 123 in the third embodiment. As illustrated in FIG. 12, in the reconstruction condition setting area 144, there is provided a high precision/short time mode 216 for choosing any of the high-precision mode and the short-time mode, when the operator selects the automatic weight determination mode 124. The configurations beside this point are the same as those in FIG. 3.

When the operator chooses the short-time mode in the high-precision/short-time mode 216, similar to the second embodiment, the large FOV weight selector 151 and the small FOV weight selector 154 select the type of the weight, in response to the operator's selection in the automatic weight determination mode 124 or in the manual weight determination mode 125.

When the operator chooses the high-precision mode in the high-precision/short-time mode 216, the large FOV weight selector 151 firstly selects the statistical value weight as the weight W(i) used for correcting the large FOV image, and repeats the iterative approximate reconstruction $k_1$ times (step 182 in FIG. 6), being a predetermined sufficiently large update count. Then, the large FOV weight selector changes the weigh W(i) used for the correction to the constant value weight, and repeatedly executes the iterative approximate reconstruction $k_2$ times being the update count smaller than $k_1$ times.

With this configuration, the quantum noise, circuit noise, and streak artifact of the background image in the large FOV image may be reduced, and further the beam hardening effect of the background image, errors in the incomplete reconstruction, and errors in the reference correction may also be reduced. Then, any various types of errors occurring in the large FOV image may be reduced, by utilizing advantages of both the statistical value weight and the constant value weight.

In this case, firstly, the statistical value weight is used as the weight, subsequently the constant value weight is used, and the update counts $k_1$ and $k_2$ are set to be $k_1 > k_2$. The reason for those settings are as the following.

In the iterative approximate reconstruction method, low-frequency components of the CT image are mainly corrected during the early stage of updating where the update count is small, irrespective whether the type of weight is the statistical value weight or the constant value weight. The low-frequency component has the characteristics causing the CT value of the image to vary gradually, resulting in that an average value of the CT values within the ROI undergoes large fluctuation. Representative examples of the low-frequency component may be the beam hardening effect, errors in the incomplete reconstruction, and errors in the reference correction. On the other hand, high-frequency components of the CT image are mainly corrected during the later stage of updating where the update count is large. Representative examples of the high-frequency component may be errors having the characteristics causing the CT value to change abruptly, such as correction of edge part of a structural object, quantum noise, and emphasis on streak artifact.

In correcting the image, when noise or errors of the low-frequency and high-frequency components are included in the image, the variation of the low-frequency and high-frequency components may act to reduce such noise or errors, whereas if there is neither noise nor errors being included in the image, there may be actions to generate noise or errors of low-frequency and high-frequency components.

Therefore, when a small update count is set with the use of the statistical value weight firstly, quantum noise and streak artifact being the high-frequency components are not reduced. On the other hand when a sufficiently large update count is set with the use of the statistical value weight, it is possible to reduce the quantum noise and streak artifact being the high-frequency components. After this correction is performed firstly using the statistical value weight as described above and a small update count is set with the use of the constant value weight, it is possible to restrain lowering of the CT value precision, due to the beam hardening effect, errors in the incomplete reconstruction, and errors in the reference correction, being low-frequency components. However, if the updating is continued until reaching a sufficiently large update count, with the use of the constant value weight, this may cause change in the high-frequency components being once reduced by the correction using the statistical value weight, and in some cases, this may increase the quantum noise, circuit noise, and streak artifact which are high-frequency components.

When a small update count is set with the use of the constant value weight firstly, it is possible to reduce the beam hardening effect being the low-frequency component. However, when a sufficiently large update count is set with the use of the constant value weight, it is difficult to sufficiently reduce the streak artifact. As thus described, when a small update count is set with the use of the statistical value weight, after the correction using the constant value weight, this may cause change in the low-frequency components once reduced, and this change may adversely act to emphasize and increase the beam hardening effect. Accordingly, though updating is performed until a sufficiently large update count with the use of the statistical value weight and the streak artifact of high-frequency component is reduced, thus increased beam hardening effect of low-frequency component may fail to be reduced.

Therefore, in the third embodiment, firstly the statistical value weight is used to perform the iterative approximate reconstruction with the large update count $k_1$, and subsequently, the constant value weight is used to perform the iterative approximate reconstruction with the small update count $k_2$. With this configuration, it is possible to utilize the advantages of both the statistical value weight and the constant value weight against the various types of errors that may occur in the large FOV image, thereby reducing the streak artifact and the beam hardening effect.

Similarly as for the small FOV, the small FOV weight selector 154 firstly performs the iterative approximate reconstruction with the use of the statistical value weight with a large update count $k_3$, and subsequently, performs the iterative approximate reconstruction with a small update count $k_4$ with the use of the constant value weight. With this configuration, the streak artifact and the beam hardening effect may further be reduced.

In the third embodiment, an explanation has been provided as to changing the type of the weight in the middle of the iterative approximate reconstruction, for both of the large FOV image and the small FOV image. It is further possible to configure such that only for either one of the large FOV image and the small FOV image, the type of the weight is changed in the middle of the iterative approximate reconstruction, and for the remaining FOV image, either of the statistical value weight and the constant value weight is used.

In the third embodiment, the change of the weight for the large FOV image and the small FOV image has been explained individually. However, the correction of the large FOV image may act to restrain the lowering of precision of the local measured projection data, and the correction of the small FOV image may produce an effect to restrain the lowering of the CT value precision. As thus described, the operation and effect caused by the change of weight may be different depending on the case of the large FOV image or the small FOV image.

An experiment was conducted to validate the utility of the third embodiment. The phantom targeted for the imaging was a human body phantom simulating the pelvis. The human body phantom being used had a structure with the CT values being close to those of living tissue.

FIG. 13(a) and FIG. 13(b) illustrate the results of the reconstruction. FIG. 13(a) illustrates the image that was obtained by performing the iterative approximate reconstruction with the update count of 10 times, using the constant value weight for correcting the large FOV image, and performing the iterative approximate reconstruction with the update count of 20 times, using the statistical value weight for correcting the small FOV image. On the other hand, the FIG. 13(b) illustrates the image that was obtained by performing the iterative approximate reconstruction with the update count of 10 times, using the constant value weight for correcting the large FOV image, and performing the iterative approximate reconstruction with the update count of 20 times, using the statistical value weight for correcting the small FOV image, and thereafter, changing the weight to the constant value weight, and performing the iterative approximate reconstruction with the update count of one time. The iterative approximate reconstruction was performed according to the OS-SPS employing the publicly known subset method, and the number of subsets was equal to 24. In FIGS. 13(a) and (b), WL was equal to 0 [HU], and WW was equal to 400 [HU]. The large FOV was equal to 550 [mm], the small FOV was equal to 250 [mm], and the center of the reconstruction of the small FOV image was set to be the position at 80 [mm] in the X-direction and at 130 [mm] in the Y-direction from the rotation center.

The images of FIG. 13(c) and FIG. 13(d) were obtained by taking a difference between a result of the FBP method being a conventional analytical construction method, and the images of FIG. 13(a) and FIG. 13(b). In FIG. 13(c) and FIG. 13(d), WL was equal to 0 [HU], and WW was equal to 100 [HU].

The dotted line 221 as shown in FIG. 13(a) and FIG. 13(c) indicates a boundary between the complete acquisition region and the incomplete acquisition region 222. Explanations of the complete acquisition region and the incomplete acquisition region 222 are the same as those given in the second embodiment.

In the present embodiment, the CT value precision of the incomplete acquisition region 222 is not evaluated, and only the CT value precision of the complete acquisition region is evaluated.

As a result of the evaluation, a difference between FIG. 13(a) and FIG. 13(b) is not clear, but the image as shown in FIG. 13(c) shows the lowering of the CT value precision, primarily caused by the low-frequency components at the point indicated by the arrows. On the other hand, in the image as shown in FIG. 13(d), it is found that lowering of the CT value precision primarily caused by the low-frequency components was restrained, and the beam hardening effect, errors in incomplete reconstruction, and errors in reference correction were reduced. Accordingly, it has been validated that the method of the third embodiment is effective, where the weight used for correcting the small FOV image is changed from the statistical value weight to the constant value weight.

In the present embodiment, explanations have been provided on the basis of the magnitude of the update count. Here, it is a matter of course that the higher is the correcting speed for every update count, the smaller value is sufficient as the update count.

<Fourth Embodiment>

Next, as the fourth embodiment, an explanation will be provided as to the X-ray CT apparatus installing software of the iterative approximate reconstruction, which is obtained by modifying a part of the first embodiment.

The X-ray CT apparatus of the fourth embodiment is different from the first embodiment, the second embodiment, and the third embodiment, in the point that the X-ray CT apparatus is provided with a correction necessity determination part 231 that determines whether or not it is necessary to correct the large FOV image according to the iterative approximate reconstruction. With this configuration, if it is not necessary to correct the large FOV image, the calculation amount is not increased by performing the iterative approximate reconstruction, and it is still possible to restrain the lowering of the CT value precision in the small FOV image. Hereinafter, the essential portion of the X-ray CT apparatus of the fourth embodiment will be explained. The configurations other than the essential portion are the same as those of the X-ray CT apparatus explained in the first embodiment, the second embodiment, and the third embodiment, and tedious explanations will not be provided.

Figure 14:
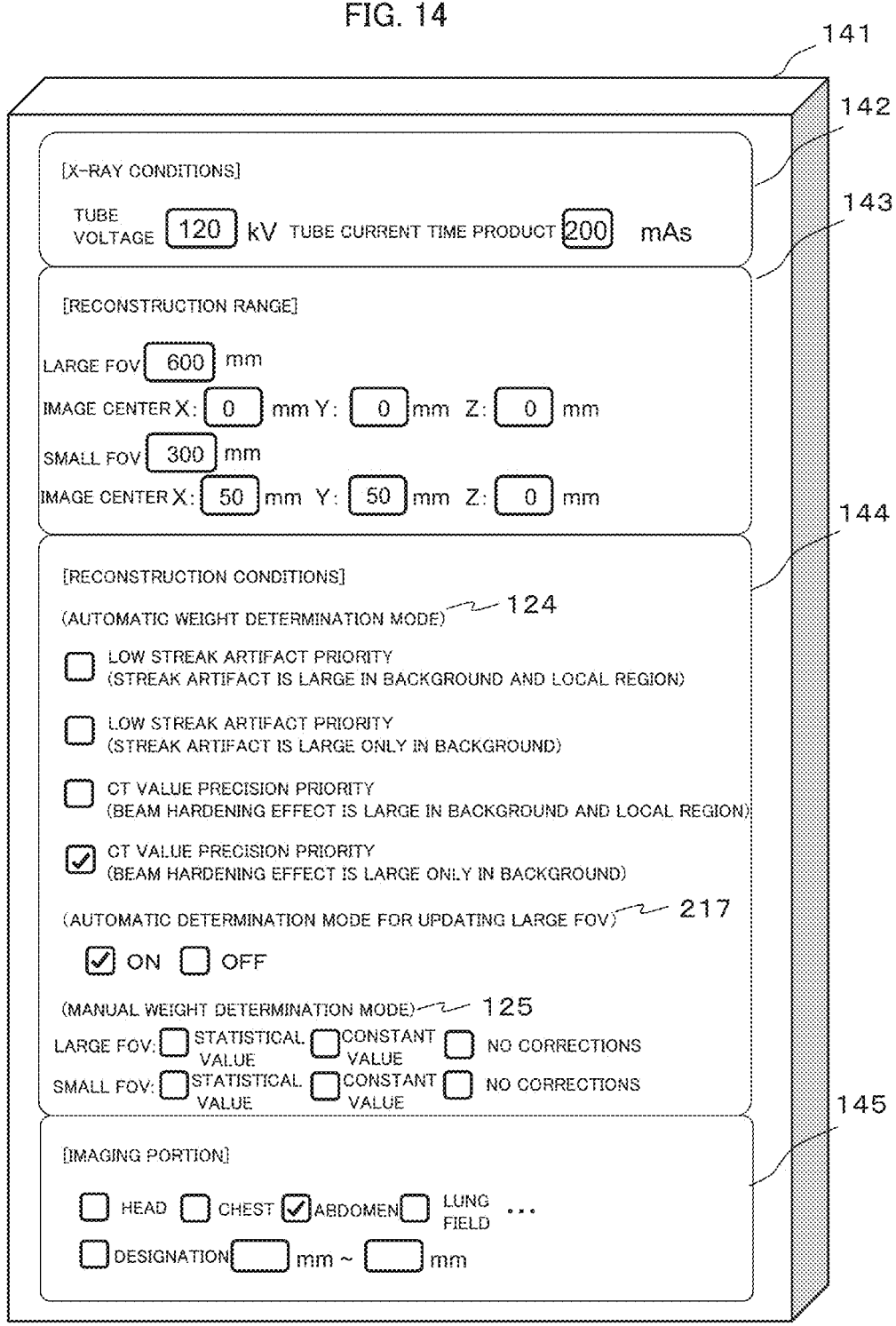
FIG. 14 illustrates the input screen of the imaging condition input part in the fourth embodiment.

FIG. 14 illustrates the imaging condition accepting screen 141 that is displayed in the monitor 123 according to the fourth embodiment. As shown in FIG. 14, in the case where the operator chooses the automatic weight determination mode 124 in the reconstruction condition setting area 144, the automatic determination mode for updating the large FOV 217 is also selectable, in addition to the automatic determination mode 124. At this time, the operations when the operator chooses OFF as the automatic determination mode for updating the large FOV 217, are the same as those described in the first embodiment, the second embodiment, and the third embodiment. Hereinafter, detailed explanation will be provided for the case where the operator chooses ON as the automatic determination mode for updating the large FOV 217.

Figure 15:
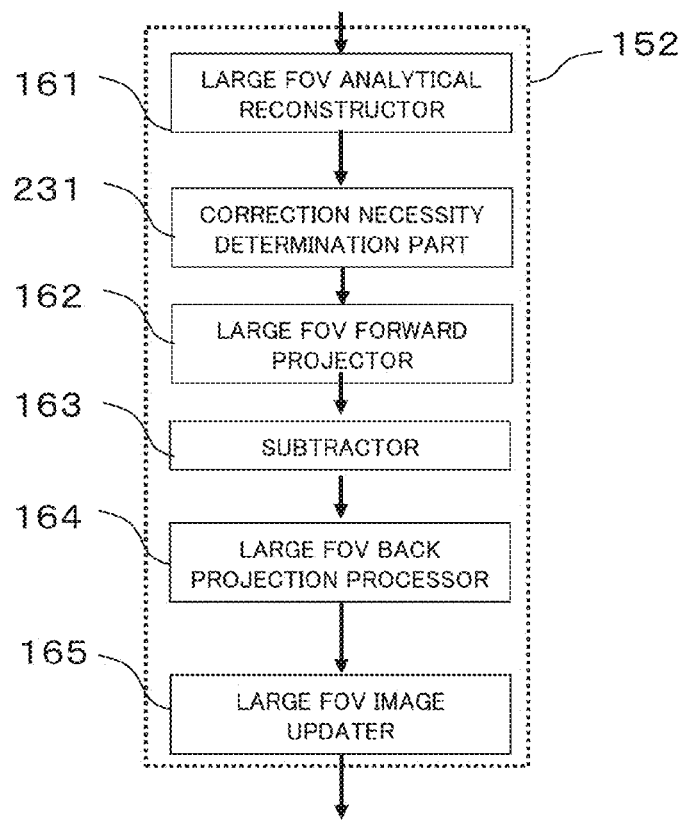
FIG. 15 is a functional block diagram illustrating the functions of the first approximate reconstructor 152 in the fourth embodiment.
Figure 16:
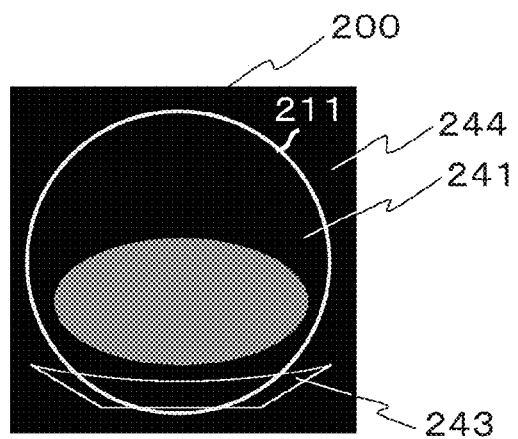
FIG. 16 illustrates a complete acquisition region and an incomplete acquisition region of the large FOV image in the fourth embodiment.

FIG. 15 illustrates the configuration of the first iterative approximate reconstructor 152, according to the fourth embodiment. The first iterative approximate reconstructor 152 is provided with a correction necessity determination part 231. The functional blocks other than this part are the same as those of FIG. 5. The correction necessity determination part 231 searches the large FOV image reconstructed by the large FOV analytical reconstructor 161 for the incomplete acquisition region 244 as shown in FIG. 16, and determines whether or not the incomplete acquisition region 244 includes any structural object other than the air, or streak artifact. In FIG. 16, the complete acquisition region 241 corresponds to a region within the circle 211 that acquires the projection data at the projection angles for one rotation, and the incomplete acquisition region 244 corresponds to a region outside the complete acquisition region 241, and the projection data is not acquired at some projection angles.

When no structural object or streak artifact exists within the incomplete acquisition region 244, the calculated projection data of the large FOV image coincides well with the measured projection data, even though the iterative approximate reconstruction is not performed. When any structural object or streak artifact exists within the incomplete acquisition region 244, it is desirable that the first iterative approximate reconstructor 152 performs the iterative approximate reconstruction, so as to improve a degree of coincidence between the measured projection data and the calculated projection data of the large FOV image.

Therefore, when there is neither structural object nor streak artifact within the incomplete acquisition region 244, the correction necessity determination part 231 determines that no correction is necessary, and transfers the large FOV image without any change as generated by the large FOV analytical reconstructor 161, to the background image generator 167. With this configuration, it is possible to reduce the calculation amount used in the iterative approximate reconstruction. On the other hand, when there is any structural object or streak artifact within the incomplete acquisition region 244, the correction necessity determination part 231 transfers the large FOV image to the large FOV forward projector 162, enabling the iterative approximate reconstruction to be executed.

Therefore, it is necessary for the correction necessity determination part 231 to determine a target such as the structural object or the streak artifact from the large FOV image. By way of example, there is a method to discriminate the region of air from the region other than the air, assuming that the incomplete acquisition region 244 of the large FOV image is filled with the air. For this determination, an image processing technique will be employed, such as publicly known threshold determination and region growing method. By way of example, the threshold TH=−950 [HU] of CT value data is set manually or automatically, and it is determined that the region with the CT value data being less than TH corresponds to the region of the air, and the region being equal to or higher than TH corresponds to the region other than the air. As shown in FIG. 16, in the large FOV image within the large FOV 200, as a result of the threshold determination on the incomplete acquisition region 244, if a part of the table 243 exists in the incomplete acquisition region 244, the correction necessity determination part 231 determines that correction of the large FOV image is necessary.

In addition to using the threshold of the CT value, it is possible to employ another way to combine the region growing method, with the shape information, positional information, and the like, of a processing target such as the table 243 captured in advance. In the present embodiment, the table 243 is assumed as the processing target as one example, but the present embodiment is not limited to this example, and streak artifact, the subject to be imaged, or the like, may be determined as the processing target.

As described above, if it is not necessary to correct the large FOV image, lowering of the CT value precision of the small FOV image may be restrained, without increasing an extra amount of calculation.

<Fifth Embodiment>

Next, as the fifth embodiment, an explanation will be provided as to the X-ray CT apparatus installing the iterative approximate reconstruction software, which is obtained by modifying a part of the fourth embodiment.

The X-ray CT apparatus of the fifth embodiment is different from the fourth embodiment in the point that the correction necessity determination part 231 searches for the measured projection data of the detection elements on the edge of the X-ray detector 2 in the channel direction, thereby determining existence of a structural object within the incomplete acquisition region 244. Hereinafter, the essential portion of the X-ray CT apparatus according to the fifth embodiment will be explained. Since the configurations other than this portion are the same as those explained in the first, the second, the third, and the fourth embodiments, tedious explanations will not be provided.

Figure 17:
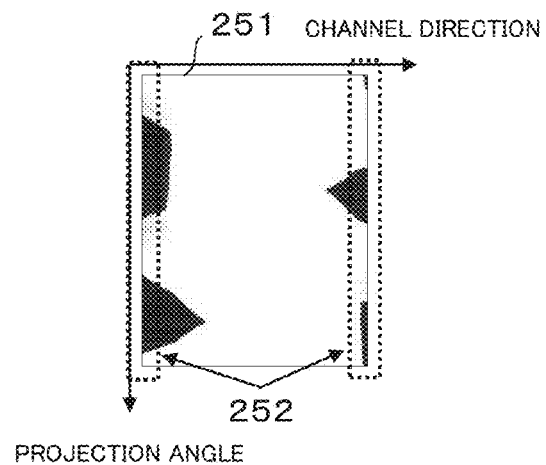
FIG. 17 illustrates an edge region of the X-ray detector and the measured projection data in the fifth embodiment.

As shown in FIG. 17, the correction necessity determination part 231 searches for the measured projection data 251 that is outputted from the correction processor 135, and when the output value (integral value of the CT value data) at the edge regions 252 of the X-ray detector 2 in the channel direction is equal to or larger than a threshold, it is determined that any structural object or the streak artifact exists in the incomplete acquisition region 244. When the output value of the measured projection data 251 at the edge regions 252 of the X-ray detector 2 is less than the threshold, it is determined that there is no structural object or streak artifact in the incomplete acquisition region 244. The threshold may be set to TH=50 [HU], for instance, and if the output value is less than TH, it is determined that the air exists, and if it is equal to or larger than TH, it is determined that there is a structural object other than the air.

In the measured projection data 251 as shown in FIG. 17, the horizontal axis indicates the projection data in the channel direction, and the vertical axis indicates the projection angle, covering the range of the projection angle from 0 to 360 degrees in the present embodiment. In the measured projection data 251 as shown in FIG. 17, the larger is the measured projection data value (the output value of the X-ray detector 2) caused by a structural object, and the like, the whiter becomes the displayed data, whereas the smaller is the measured projection data value, the more gray becomes the data.

The edge regions 252 of the X-ray detector 2 incorporate five detector elements on each of both sides. It is further possible to use the data obtained by subjecting the output values of the five detection elements on each side to an averaging process, so as to determine whether the output value from the edge regions 252 is equal to or larger than the threshold. This may reduce the noise effect being random components, and prevent erroneous decision.

When the correction necessity determination part 231 determines that there is no existence of structural object, or the like, in the incomplete acquisition region 244, the iterative approximate reconstruction process is not performed and the large FOV image is transferred to the background image generator 167. Accordingly, it is possible to skip correcting the large FOV image, and restrain the lowering of the CT value precision of the small FOV image, without increasing an extra amount of calculation.

In the present embodiment, the correction necessity determination part 231 is configured subsequent to the large FOV analytical reconstructor 161, but it may be placed prior to the large FOV analytical reconstructor 161.

<Sixth Embodiment>

Next, as the sixth embodiment, an explanation will be provided as to the X-ray CT apparatus employing a conventional iterative approximate reconstruction method without using the extensive reconstruction technique, and having a configuration, similar to the third embodiment that changes the type of the weight in the middle of the iterative approximate reconstruction.

Figure 18:
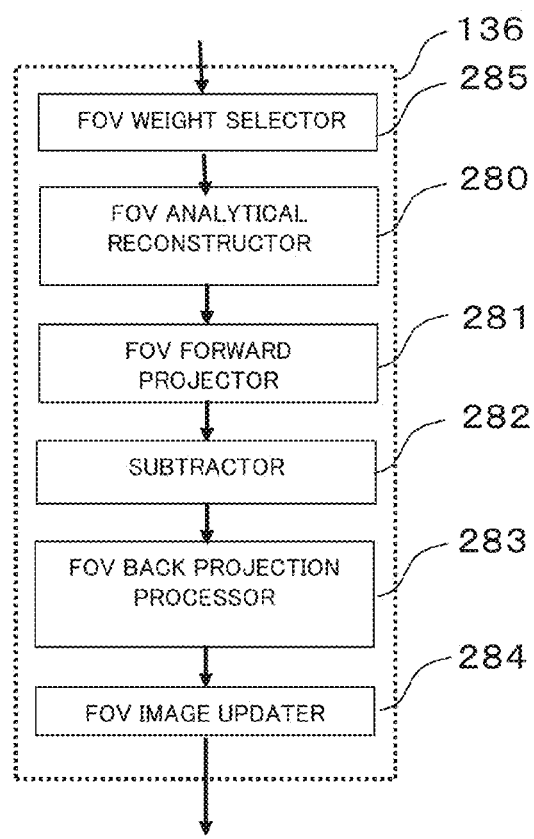
FIG. 18 is a functional block diagram for explaining the function of the reconstruction processor 136 in the sixth embodiment.

This X-ray CT apparatus has a configuration being the same as the first embodiment as shown in FIG. 1 and FIG. 2, but the reconstruction processor 136 in FIG. 2 has the configuration as shown in FIG. 18, since the conventional iterative approximate reconstruction is performed. In other words, the reconstruction processor 136 incorporates an FOV weight selector 285 configured to select the weight W(i) used in the iterative approximate reconstruction of an FOV image, an FOV analytical reconstructor 280, an FOV forward projector 281, a subtractor (data comparator) 282, an FOV back projection processor 283, and an FOV image updater 284. Functions and operations of those elements correspond respectively to the large FOV weight selector 151, the large FOV analytical reconstructor 161, the large FOV forward projector 162, the subtractor 163, the large FOV back projection processor 164, and the large FOV image updater 165 as shown in FIG. 9, and those elements perform the iterative approximate reconstruction on the FOV image.

In this case, similar to the large FOV weight selector 151 of the third embodiment, the FOV weight selector 285 of FIG. 18 firstly selects the statistical value weight as the weight W(i) used for correcting the FOV image (large FOV image), repeats the iterative approximate reconstruction $k_1$ times being the predetermined update count sufficiently large, thereafter changes the weight W(i) used for the correction to the constant value weight, and repeatedly executes the iterative approximate reconstruction $k_2$ times being the update count smaller than $k_1$ times.

With this configuration, quantum noise, circuit noise, and streak artifact in the FOV image may be reduced, and also beam hardening effect, errors in the incomplete reconstruction, and errors in the reference correction of the FOV image may also be reduced. Therefore, various types of errors that occur in the FOV image may be reduced by using the advantages of both the statistical value weight and the constant value weight. Details of the foregoing are the same as those described in the third embodiment.

It is further possible to configure the functional block for performing the iterative approximate reconstruction of the present embodiment, as the third iterative approximate reconstructor that is provided in the X-ray CT apparatus of the first, the second, the third, the fourth, and the fifth embodiments. In this case, the first and the second iterative approximate reconstructors 152 and 155 in the first to the fifth embodiments, and the third iterative approximate reconstructor of the sixth embodiment may be selectively employed, depending on the instruction from the operator.

In order to validate the utility of the present embodiment, an experiment was conducted. The phantom targeted for the imaging was a human body phantom simulating the pelvis, and it was additionally wrapped by a phantom made of polyethylene material. The human body phantom being used had a structure with the CT values being close to those of living tissue.

FIG. 19(a) and FIG. 19(b) illustrate results of the reconstruction. FIG. 19(a) illustrates the image obtained by subjecting the FOV image to the iterative approximate reconstruction, using the statistical value weight for the correction, and setting the update count to be 100 times. On the other hand, FIG. 19(b) illustrates the image obtained by performing the iterative approximate reconstruction using the statistical value weight, setting the update count to 100 times, thereafter changing the weight to the constant value weight and performing the iterative approximate reconstruction setting the update count to 3 times. In the image reconstruction as shown in FIG. 19(a) and FIG. 19(b), the OS-SPS using a publicly known subset method was employed, and the number of the subsets was set to be 24. In FIG. 19(a) and FIG. 19(b), WL was equal to 0 [HU], WW was equal to 400 [HU], and the FOV was equal to 550 [mm].

FIG. 19(c) and FIG. 19(d) illustrate the images obtained by taking a difference between a result of the FBP method being a conventional analytical reconstruction method, and the results of the iterative approximate reconstruction method as shown in FIG. 19(a) and FIG. 19(b). In FIG. 19(c) and FIG. 19(d), WL was equal to 0 [HU], and WW was equal to 100 [HU].

The dotted line 261 shown in FIG. 19(a) and FIG. 19(c) indicates a boundary between the complete acquisition region and the incomplete acquisition region. The complete acquisition region and the incomplete acquisition region are the same as those in the second embodiment and in the fourth embodiment.

In the present embodiment, only the CT value precision of the complete acquisition region is evaluated, without reference to the CT value precision of the incomplete acquisition region.

As a result of the evaluation, there is not obvious difference between FIG. 19(a) and FIG. 19(b), but in the image of FIG. 19(c), there is found lowering of the CT value precision primarily caused by the low-frequency components in the points indicated by the arrows. In the image in FIG. 19(d), however, it is found that the lowering of the CT value primarily caused by the low-frequency components was successfully restrained, enabling reduction of the beam hardening effect, errors in the incomplete reconstruction, and errors in the reference correction. As shown in the sixth embodiment, it is validated that even when the conventional iterative approximate reconstruction is performed, changing the weight from the statistical value weight to the constant value weight is effective for reducing errors.

In the present embodiment, explanations have been provided on the basis of the magnitude of the update count. Here, it is a matter of course that the higher is the correcting speed for every update count, the smaller value is sufficient as the update count.

EXPLANATION OF REFERENCES

1 . . . X-ray tube, 2 . . . X-ray detector, 3 . . . gantry, 4 . . . rotating plate, 5 . . . table, 6 . . . imaging target, 7 . . . circular opening, 101 . . . input part, 102 . . . imager, 103 . . . image generator, 111 . . . keyboard, 112 . . . mouse, 113 . . . memory, 114 . . . CPU, 115 . . . HDD device, 116 . . . gantry controller, 117 . . . X-ray controller, 118 . . . table controller, 119 . . . DAS, 120 . . . memory, 121 . . . CPU, 122 . . . HDD device, 123 . . . monitor, 131 . . . imaging condition input part, 132 . . . imaging controller, 133 . . . imager, 134 . . . signal acquisition part, 135 . . . correction processor, 136 . . . reconstruction processor, 137 . . . image display part, 141 . . . imaging condition accepting screen, 142 . . . X-ray condition setting area, 143 . . . reconstruction range setting area, 144 . . . reconstruction condition setting area, 145 . . . imaging portion setting area, 151 . . . large FOV weight selector, 152 . . . the first iterative approximate reconstructor, 153 . . . local measured projection data extractor, 154 . . . small FOV weight selector, 155 . . . the second iterative approximate reconstructor, 161 . . . large FOV analytical reconstructor, 162 . . . large FOV forward projector, 163 . . . subtractor (data comparator), 164 . . . large FOV back projection processor, 165 . . . large FOV image updater, 167 . . . background image generator, 168 . . . background image forward projector, 169 . . . subtractor (data comparator), 170 . . . small FOV analytical reconstructor, 171 . . . small FOV forward projector, 172 . . .

subtractor (data comparator), 173 . . . small FOV back projection processor, 174 . . . small FOV image updater, 211 . . . boundary between complete acquisition region and incomplete acquisition region, 212 . . . small FOV, 213 . . . upper-layer region of interest, 214 . . . middle-layer region of interest, 215 . . . lower-layer region of interest, 231 . . . large FOV weight selector, 241 . . . complete acquisition region, 244 . . . incomplete acquisition region, 243 . . . table, 251 . . . measured projection data, 252 . . . edge region

What is claimed is:

1. An X-ray CT apparatus comprising;
an X-ray generator configured to generate X-rays;
an X-ray detector configured to detect the X-rays after passing through a subject and obtain measured projection data;
a rotating plate configured to mount the X-ray generator and the X-ray detector thereon, and rotate around the subject;
a local measured projection data extractor configured to reconstruct a first CT image relating to a first reconstruction range of the subject, from the measured projection data obtained by the X-ray detector, and use the first CT image to extract from the measured projection data, local measured projection data in association with a second reconstruction range within the first reconstruction range; and
a second iterative approximate reconstructor configured to reconstruct a second CT image relating to the second reconstruction range, from the local measured projection data, and performs iterative correction on the second CT image, so that local calculated projection data obtained by subjecting the second CT image to forward projection by calculation, becomes equal to the local measured projection data extracted by the local measured projection data extractor,
wherein, the local measured projection data extractor comprising a first iterative approximate reconstructor configured to perform the iterative correction on the first CT image, so that calculated projection data obtained by subjecting the first CT image to the forward projection by calculation becomes equal to the measured projection data detected by the X-ray detector, and use the first CT image iteratively corrected so as to extract the local measured projection data in association with the second reconstruction range; and
wherein, the local measured projection data extractor comprises a first weight selector configured to select a weight to be used for the iterative correction on the first CT image, and the second iterative approximate reconstructor comprises a second weight selector configured to select a weight to be used for the iterative correction on the second CT image,
wherein, each of the first weight selector and the second weight selector selects either one of a statistical value weight and a constant value weight, the statistical value weight being various weight to be given to output data from plural detection elements constituting the X-ray detector, in response to magnitude of the output, and the constant value weight being an identical weight to be given to the output data from the plural detection elements.

2. The X-ray CT apparatus according to claim 1, wherein the local measured projection data extractor comprises;
a background image generator configured to generate a background image that is obtained by eliminating pixels of the second reconstruction range from the first CT image that is iteratively corrected by the first iterative approximate reconstructor,
a background image forward projector configured to subject the background image to the forward projection to obtain background projection data, and
a subtractor configured to subtract the background projection data from the measured projection data detected by the X-ray detector to obtain the local measured projection data.

3. The X-ray CT apparatus according to claim 1, further comprising;
an input part configured to accept designation of the weight from an operator,
wherein, each of the first weight selector and the second weight selector select either one of the statistical value weight and the constant value weight, in response to the designation accepted by the input part.

4. The X-ray CT apparatus according to claim 3, wherein when the input part accepts from the operator an instruction to place priority to reducing streak artifact, the first weight selector and the second weight selector select the statistical value weight, whereas when the input part accepts from the operator an instruction to place priority to CT value precision, the first weight selector and the second weight selector select the constant value weight.

5. The X-ray CT apparatus according to claim 4, wherein either of the first weight selector and the second weight selector selects the statistical value weight, and the other selector selects the constant value weight.

6. The X-ray CT apparatus according to claim 3, wherein the input part is allowed to accept from the operator a designation to perform the iterative correction with switching a type of the weight, at least one of the first iterative approximate reconstructor and the second iterative approximate reconstructor performs the iterative correction twice with switching the type of the weight, and a first iterative correction uses the statistical value weight, a second iterative correction uses the constant value weight, and an update count of the first iterative correction is larger than the update count of the second iterative correction.

7. The X-ray CT apparatus according to claim 1, wherein at least one of the first iterative approximate reconstructor and the second iterative approximate reconstructor performs the iterative correction twice with switching a type of the weight, and a first iterative correction uses the statistical value weight, a second iterative correction uses the constant value weight, and an update count of the first iterative correction is larger than the update count of the second iterative correction.

8. The X-ray CT apparatus according to claim 1, wherein the local measured projection data extractor further comprises a correction necessity determination part configured to determine whether or not the iterative correction is necessary, according to the first CT image that is reconstructed from the measured projection data obtained by the X-ray detector, and when the correction necessity determination part determines that the iterative correction is necessary, the first iterative approximate reconstructor performs the iterative correction on the first CT image.

9. The X-ray CT apparatus according to claim 8, wherein the correction necessity determination part searches an incomplete acquisition region for existence of any structural object, the incomplete acquisition region being outside a complete acquisition region of the first CT image that is reconstructed from the measured projection data obtained by the X-ray detector, and determines whether or not the iterative correction is necessary on the basis of a result of the searching.

10. The X-ray CT apparatus according to claim 8, wherein the correction necessity determination part determines whether or not the iterative correction is necessary, depending on an output value from the detection element on the edge of the X-ray detector.

11. The X-ray CT apparatus according to claim 1, further comprising;
- a third iterative approximate reconstructor configured to reconstruct the first CT image relating to the first reconstruction range of the subject, from the measured projection data obtained by the X-ray detector, and perform the iterative correction on the first CT image, so that the calculated projection data obtained by subjecting the first CT image to the forward projection by calculation, becomes equal to the measured projection data detected by the X-ray detector,
- wherein, the third iterative approximate reconstructor has a configuration that the iterative correction is performed twice with switching a type of the weight, a first iterative correction uses a statistical value weight being various weight to be given to output data from plural detection elements, in response to magnitude of the output from the plural detection elements constituting the X-ray detector, a second iterative correction uses a constant value weight being an identical weight to be given to the output data from the plural detection elements, and an update count of the first iterative correction is larger than the update count of the second iterative correction.

12. An X-ray CT apparatus, comprising;
- an X-ray generator configured to generate X-rays;
- an X-ray detector configured to detect the X-rays after passing through a subject and obtain measured projection data;
- a rotating plate configured to mount the X-ray generator and the X-ray detector thereon, and rotate around the subject; and
- an iterative approximate reconstructor configured to reconstruct a CT image relating to a predetermined reconstruction range of the subject, from the measured projection data, and performs iterative correction on the CT image, so that calculated projection data obtained by subjecting the CT image to forward projection by calculation, becomes equal to the measured projection data obtained by the X-ray detector, the iterative approximate reconstructor performing the iterative correction twice with switching a type of a weight; and
- wherein, the iterative approximate reconstructor uses a statistical value weight in the first iterative correction out of the twice iterative corrections, the statistical value weight being various weight to be given to output data from plurality detection elements, in response to magnitude of the output from the plurality detection elements constituting the X-ray detector, and uses a constant value weight in the second iterative correction, the constant value weight being an identical weight to be given to the output data from the plural detection elements, and an update count of the first iterative correction is larger than the update count of the second iterative correction.

13. An X-ray CT image processing method, comprising;
- reconstructing a first CT image of a first reconstruction range from projection data of a subject, the projection data being measured by an X-ray detector of an X-ray CT apparatus;
- using the first CT image to extract local measured projection data in association with a second reconstruction range within the first reconstruction range, from the projection data being measured, and generating a second CT image relating to the second reconstruction range, from the local measured projection data;
- performing iterative correction on the first CT image so that the first calculated projection data obtained from the first CT image by projection calculation becomes equal to the projection data of the subject;
- using the first CT image after the iterative correction is performed, so as to extract the local measured projection data in association with the second reconstruction range; and
- performing the iterative correction on the second CT image, so that the local measured projection data being extracted becomes equal to the second calculated projection data obtained from the second CT image by the projection calculation;
- selecting a first weight to be used for the iterative correction on the first CT image,
- selecting a second weight to be used for the iterative correction on the second CT image, and
- wherein, the first weight and second weight include one of a statistical value weight and a constant value weight, the statistical value weight being various weight to be given to output data from plurality of detection elements constituting the X-ray detector, in response to magnitude of the output, and the constant value weight being an identical weight to be given to the output data from the plurality detection elements.

* * * * *